United States Patent
Chen et al.

(10) Patent No.: US 7,745,134 B2
(45) Date of Patent: Jun. 29, 2010

(54) PREDICTING POST-TREATMENT SURVIVAL IN CANCER PATIENTS WITH MICRORNAS

(75) Inventors: Jian-Wei Chen, Fongyuan (TW); Sung-Liang Yu, Taipei (TW); Hsuan-Yu Chen, Taipei (TW); Gee-Chen Chang, Taichung (TW); Chih-Yi Chen, Taichung (TW); Pan-Chyr Yang, Taipei (TW)

(73) Assignees: National Taiwan University, Taipei (TW); Taichung Veterans General Hospital, Taichung (TW); National Chung Hsing University, Taichung (TW)

( * ) Notice: Subject to any disclaimer, the term of this patent is extended or adjusted under 35 U.S.C. 154(b) by 0 days.

(21) Appl. No.: 12/100,113

(22) Filed: Apr. 9, 2008

(65) Prior Publication Data

US 2008/0254473 A1    Oct. 16, 2008

Related U.S. Application Data

(60) Provisional application No. 60/910,993, filed on Apr. 10, 2007.

(51) Int. Cl.
  *C12Q 1/68*  (2006.01)
  *C12P 19/34* (2006.01)
(52) U.S. Cl. .......................... 435/6; 435/91.1; 435/91.2
(58) Field of Classification Search ........................ None
  See application file for complete search history.

(56) References Cited

U.S. PATENT DOCUMENTS

| | | |
|---|---|---|
| 2004/0152112 A1 | 8/2004 | Croce |
| 2005/0262577 A1 | 11/2005 | Guelly |
| 2005/0272067 A1 | 12/2005 | Macina |
| 2006/0078913 A1 | 4/2006 | Macina |
| 2006/0105360 A1 | 5/2006 | Croce |
| 2006/0165659 A1 | 7/2006 | Croce |
| 2007/0065844 A1 | 3/2007 | Golub |

OTHER PUBLICATIONS

Yu et al., "MicroRNA Signature Predicts Survival and Relapse in Lung Cancer," Cancer Cell, Jan. 2008, vol. 13, pp. 48-57.*
Bandres, E., et al., "*Identification by Real-time PCR of 13 mature microRNAs differentially expressed in colorectal cancer and non-tumoral tissues*". Molecular Cancer. Jul. 19, 2006, vol. 5, pp. 29-38; abstract; p. 1179, para 7.
Voorhoeve, P.M., et al., "*A genetic Screen Implicates miRNA-372 and miRNA-373 as Oncogenes in Testicular Germ Cell Tumors*". Cell. Mar. 24, 2006, vol. 124, pp. 1169-1181; Table I; p. 36, para 5.

* cited by examiner

*Primary Examiner*—Young J Kim
(74) *Attorney, Agent, or Firm*—Occhiuti Rohlicek & Tsao LLP

(57) ABSTRACT

This invention provides a method for predicting the post-treatment survival prospect of a cancer patient based on the expression level(s) of microRNAs hsa-miR137, hsa-miR372, hsa-miR182*, hsa-miR221, and hsa-let-7a in that cancer patient.

6 Claims, 3 Drawing Sheets

US 7,745,134 B2

PREDICTING POST-TREATMENT SURVIVAL IN CANCER PATIENTS WITH MICRORNAS

CROSS-REFERENCE TO RELATED APPLICATION

This application claims the benefit of U.S. Provisional Application No. 60/910,993, filed on Apr. 10, 2007, the contents of which are hereby incorporated by reference in its entirety.

BACKGROUND

Lung cancer, predominantly non-small-cell lung cancer (NSCLC), is the most common cause of cancer deaths worldwide. See Jemal et al., CA Cancer J. Clin. 56:106-130 (2006). Early-stage NSCLC patients show a relapse rate of 40% within 5 years after treatment; it is suggested that the disease stage might be a factor associated with clinical outcomes. See Miller, Am. J. Respir. Cell Mol. Biol. 33: 216-223 (2005). However, this factor alone is inadequate to predict such outcomes.

It has been suggested that gene expression profiling, in particular, microRNA profiling, is useful in both cancer diagnosis and prognosis. See Endoh et al., J. Clin. Oncol. 22:811-819 (2004); and Potti et al., N. Engl. J. Med. 355:570-580 (2006). For example, the expression patterns of certain microRNAs are found to be more accurate than the expression patterns of protein-coding genes in determining cancer subtypes. See Calin et al., Nat. Rev. Cancer 6:857-866 (2006); and Volinia et al., Proc. Natl. Acad. Sci. U.S.A. 103: 2257-2261 (2006).

MicroRNAs are small non-protein-coding RNAs that regulate the expression of hundreds of genes post-transcriptionally via RNA interference, thereby controlling a broad range of biopathways, e.g., cell proliferation, differentiation, and apoptosis. See Calin et al., 2006. Certain microRNA signatures, i.e., one or more microRNAs that display particular expression patterns in a group of patients, were reported to be associated with clinical outcomes of chronic lymphocytic leukemia, lung adenocarcinoma, breast, pancreas and cancers. See Calin et al., 2006. Identifying new microRNA signatures is of great interest, as they would be useful tools in predicting clinical outcomes of various cancers, in particular, NSCLC.

SUMMARY

This invention is based on the observation that the expression levels of certain microRNAs, such as hsa-miR137, hsa-miRNA372, hsa-miR182*, hsa-miR221 and hsa-let-7a, correlate with the post-treatment survival prospect of a cancer patient.

In one aspect, this invention provides a method for predicting post-treatment survival prospect of a cancer patient by determining a normalized threshold cycle value (−dCt) based on the expression level of hsa-miR137, hsa-miR372, hsa-miR182*, hsa-miR221, or hsa-let-7a. The patient is determined to have a fair prospect of post-treatment survival if the −dCt value of hsa-miR137, hsa-miR182*, and hsa-miR372 is equal to or lower than −8.22, −7.83, and −11.25, respectively, or if the −dCt value of hsa-miR221 and hsa-let-7a is equal to or higher than −0.57 and 2.21, respectively.

In another aspect, the post-treatment survival prospect of a cancer patient can be predicted based on the expression levels of four of the microRNAs selected from hsa-miR137, hsa-miR372, hsa-miR182*, hsa-miR221 and hsa-let-7a. More specifically, 1. When the expression levels of hsa-miR372, hsa-miR182*, hsa-miR221 and hsa-let-7a are investigated, a risk score is calculated as follows: (0.31×expression level of hsa-miR372)+(0.28×expression level of hsa-miR182*)+(−0.13×expression level of hsa-miR221)+(−0.14×expression level of hsa-let-7a). A risk score equal to or lower than −5.90 indicates that the patient has a fair prospect for post-treatment survival.

2. When the expression levels of hsa-miR137, hsa-miR182*, hsa-miR221 and hsa-let-7a are investigated, a risk score is calculated as follows: (0.15×expression level of hsa-miR137)+(0.28×expression level of hsa-miR182*)+(−0.13×expression level of hsa-miR221)+(−0.14×expression level of hsa-let-7a). A risk score equal to or lower than −3.71 indicates that the patient has a fair prospect for post-treatment survival.

3. When the expression levels of hsa-miR137, hsa-miR372, hsa-miR221 and hsa-let-7a are investigated, a risk score is calculated as follows: (0.15×expression level of hsa-miR137)+(0.31×expression level of hsa-miR372)+(−0.13×expression level of hsa-miR221)+(−0.14×expression level of hsa-let-7a). A risk score equal to or lower than −4.87 indicates that the patient has a fair prospect for post-treatment survival.

4. When the expression levels of hsa-miR137, hsa-miR182*, hsa-miR372 and hsa-let-7a are investigated, a risk score is calculated as follows: (0.15×expression level of hsa-miR137)+(0.28×expression level of hsa-miR182*)+(0.31×expression level of hsa-miR372)+(−0.14×expression level of hsa-let-7a). A risk score equal to or lower than −7.02 indicates that the patient has a fair prospect for post-treatment survival.

5. When the expression levels of hsa-miR137, hsa-miR182*, hsa-miR221 and hsa-miR372 are investigated, a risk score is calculated as follows: (0.15×expression level of hsa-miR137)+(0.28×expression level of hsa-miR182*)+(−0.13×expression level of hsa-miR221)+(0.31×expression level of hsa-miR372). A risk score equal to or lower than −6.86 indicates that the patient has a fair prospect for post-treatment survival.

In yet another aspect, the post-treatment survival prospect of a cancer patient can be predicted based on his or her expression levels of the five microRNAs mentioned above. A risk score is calculated as follows: (0.15×expression level of hsa-miR137)+(0.31×expression of hsa-miR372)+(0.28×expression level of hsa-miR182*)+(−0.13×expression level of hsa-miR221)+(−0.14×expression level of hsa-let-7a). A cancer patient has fair prospect of post-treatment survival if his or her risk score is equal to or lower than −7.1.

In still another aspect, the post-treatment survival prospect can be predicted based on the expression levels of hsa-miR221, hsa-miR372, and hsa-miR137. A risk score is calculated as follows: (0.15×expression level of hsa-miR137)+(0.31×expression of hsa-miR372)+(−0.13×expression level of hsa-miR221). A cancer patient will have a fair prospect of post-treatment survival if the risk score is equal to or lower than −4.7.

A cancer patient having "a fair prospect of post-treatment survival" means that his or her risk of post-treatment death is at least 50% (e.g., 100% or 150%) lower than the average risk of death in patients having the same type of cancer.

Also within the scope of this invention is a kit for detecting the expression of microRNAs. In one example, the kit comprises oligonucleotides capable of detecting the expression of hsa-miR221, hsa-miR372, and hsa-miR137. In another example, it comprises oligonucleotides capable of detecting the expression of at least four microRNAs selected from hsa-miR137, hsa-miR372, hsa-miR182*, hsa-miR221, and hsa-let-7a. The oligonucleotides contained in any of the just-described kits can be immobilized on a supporting member (e.g., a polymer substrate) to form nucleic acid chips.

The cancer patient who has been subjected to treatment (e.g., surgical treatment, chemical treatment, or radiotherapy) has lung cancer (e.g., non-small cell lung cancer of all stages), leukemia, breast cancer, pancreatic cancer, adenocarcinoma, or squamous cell carcinoma, colon cancer or hepatocellular carcinoma.

The details of one or more embodiments of the invention are set forth in the description below. Other features, objects, and advantages of the invention will be apparent from the description and from the claims.

DETAILED DESCRIPTION

Figure 1:
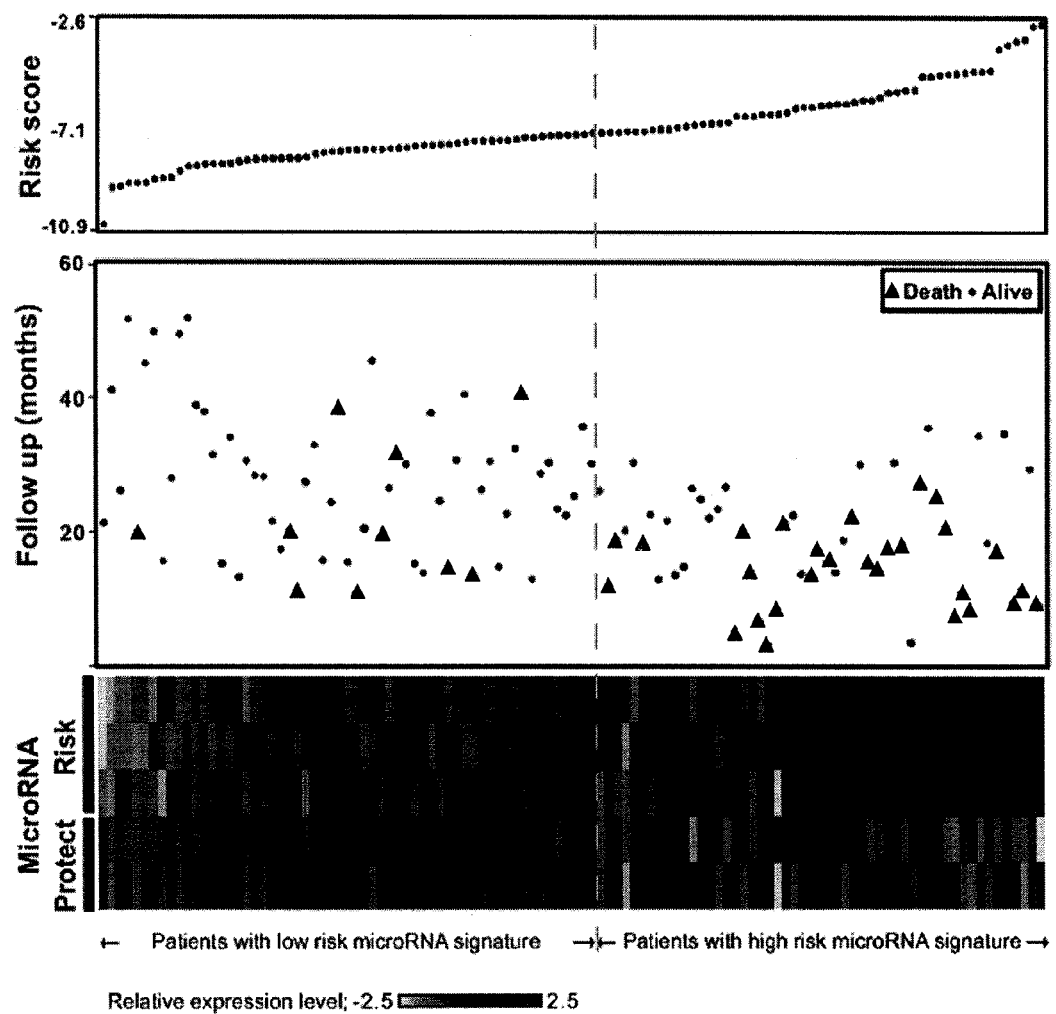
FIG. 1 is a diagram showing a microRNA risk-score analysis of 112 NSCLC patients based on the expression levels of hsa-miR137, hsa-miR372, hsa-miR182*, hsa-miR221, and hsa-let-7a in these patients. Upper panel: MicroRNA risk-score distribution. Middle panel: Patients' death/survival status. Bottom panel: Patients' microRNA expression profiles; the five rows, from bottom to top, refer to hsa-let-7a, hsa-miR221, hsa-miR372, hsa-miR182*, and hsa-miR137, respectively; the columns each represent a patient. The dotted line represents the cut-off line (risk score −7.1) dividing patients into low-risk and high-risk groups.

This application provides a method for predicting a clinical outcome (e.g., the post-treatment survival prospect) of a cancer patient based on the expression patterns of one or more microRNAs that are associated with the clinical outcome.

The one or more microRNAs associated with the outcome can be identified as follows.

A group of post-treatment cancer patients are recruited. These patients, suffering from the same type of cancer, are randomly assigned to a training group and a testing group. The expression levels of a number of microRNAs in cancer tissues/cells (e.g., contained in biopsies, formalin-fixed-paraffin-embedded tissues, or frozen tissues) are determined for the patients in both groups following methods known in the art, e.g., real-time PCR or micro-array analysis. The expression level of each microRNA thus determined is normalized by the expression level of an internal control, such as a small nuclear RNA (e.g., U1, U2, or U6), in the same patient to obtain a normalized expression level.

Normalized expression levels of the microRNAs obtained from the training group are subjected to statistical analysis, e.g., Cox regression analysis, to determine which microRNA(s) is associated with a clinical outcome (e.g., post-treatment survival) of the cancer patients. In one example, hazard ratios obtained from univariate Cox regression analysis are used to identify the microRNA(s) that is associated with death due to recurrence of cancer or any other cause. See Cox, J. Royal Statistical Society Series B 34:187-220 (1972). If the hazard ratio of a microRNA is less than 1, that microRNA is deemed as a protective microRNA, and if the hazard ratio of a microRNA is greater than 1, that microRNA is deemed as a risk microRNA.

Once the microRNAs associated with a clinical outcome (e.g., protective and risk microRNAs) are identified, the correlation between their expression patterns and a clinical outcome can be determined by statistical analysis known in the art. In one example, a risk score is calculated for each patient based on the expression levels of one or more of the protective and/or risk microRNAs, and a relationship between the value of the risk score and a patient's survival period after treatment is then determined. The correlation thus determined is verified in the testing group to confirm that the microRNA expression pattern is truly associated with the clinical outcome of interest. Preferably, this correlation is further validated in an independent cohort including a number of patients having the same type of cancer as those in the training and testing groups.

After verification, and preferably, validation, the identified microRNAs can be used to predict the clinical outcome, based on their expression patterns, in patients having the same type of cancer. For example, one can construct a mathematical formula, taking into consideration both the expression levels of these microRNAs and the significance of the statistical analysis mentioned above. Following this mathematical formula, a risk score is calculated for a patient. The value of the risk score indicates the patient's clinical outcome.

The microRNAs associated with a clinical outcome of a cancer patient can also be used to identify potential targets for cancer treatment. See Czech, N. Engl. J. Med. 354:1194-1195 (2006). Genes targeted by these microRNAs can be identified using microRNA target prediction algorithms, e.g., PicTar, see Krek et al., Nat. Genet. 37:495-500 (2005); TargetScan, see Lewis et al., Cell 115:787-798 (2003); miRNAMap, see Hsu et al., Nucleic Acids Res. 34:D135-139 (2006); miR-Base, see Griffiths-Jones et al., Nucleic Acids Res. 34:D140-144 (2006); GenMAPP, see genmapp.org; and Reactome, see reactome.org. These genes and their products are potential targets or agents for cancer therapy.

Without further elaboration, it is believed that the above description has adequately enabled the present invention. The example below shows microRNA signatures that can be used for predicting post-treatment survival prospect in NSCLC patients. This example is to be construed as merely illustrative, and not limitative of the remainder of the disclosure in any way whatsoever. All of the publications cited herein are hereby incorporated by reference in their entirety.

Materials and Methods (a) Patients and Tissue Specimens.

112 consecutive NSCLC patients, all underwent surgical resection, were recruited from the Taichung Veterans General Hospital. These patients were randomly assigned to a training dataset (n=56) and a testing dataset (n=56). In addition, 62 consecutive patients who also underwent surgical resection were recruited from National Taiwan University Hospital. These 62 patients formed an independent cohort. Frozen specimens of lung cancer tissues were obtained from all of the patients recruited for this study. All of the patients are Han Chinese.

(b) MicroRNA Profiling.

MicroRNA expression profiling was performed using ABI PRISM 7900 Real Time PCR System and TaqMan MicroRNA Assays Human Panel-Early Access Kit, which contains primers for determining 157 mature human microRNAs (Applied Biosystems). The cDNA of each microRNAs was first amplified using TaqMan MicroRNA RT reagent and primers specific for that microRNA, and further amplified using TaqMan 2× Universal PCR Master mix. During amplification, a fluorescent dye was incorporated into the cDNA product. The expression level of each microRNA, represented by a threshold cycle (Ct) value, was determined based on the level of the fluorescence generated by the fluorescent dye incorporated into the cDNA product. Ct refers to the fractional number at which the fluorescence passes a fixed threshold. The Ct value of each microRNA was then normalized by that of U6, a common internal control for microRNA quantification assays. See Jiang et al., Nucleic Acids Res. 33:5394-5403 (2005); and Yanaihara et al., Cancer Cell 9:189-198 (2006). More specifically, the normalized Ct value (–dCt) was calculated as follows: $-dCt = (Ct_{microRNA} - Ct_{U6})$.

(c) Statistical Analysis

Hazard ratios obtained from univariate Cox regression analysis were used to identify the microRNA(s) whose expression levels were associated with patient's post-treatment death/survival. To reduce false positive results, the P value of univariate Cox regression value of each microRNA was evaluated by a permutation test, wherein a patient's survival period, together with censoring status, was randomly permuted for a total of 10,000 iterations.

A mathematical formula was constructed for calculating a risk store for each patient. The formula took into account both the expression levels of one or more of the microRNAs that were identified to be associated with post-treatment death/survival and the regression coefficients derived from the aforementioned univariate Cox regression analyses. See Lossos et al., N. Engl. J. Med. 350:1828-1837; and Cox, 1972. The risk score of a patient correlates with the patient's post-treatment survival period: patients having high risk scores are expected to have shorter survival periods after treatment and patients having low risk scores are expected to live longer after treatment.

All of the patients subjected to this study were assigned to a high-risk group and a low-risk group based on their risk scores. The differences in patient characteristics between the high-risk group and the low-risk group were analyzed using Student's t test for continuous variables or Fisher's exact test for categorical variables. The Kaplan-Meier method was used to estimate the overall survival and relapse-free survival for patients in both groups. The differences as to the overall and replapse-free survival between patients in the two groups were analyzed using the log-rank test. All results thus obtained from the training dataset were validated in patients in the testing dataset and patients in the independent cohort.

Multivariate Cox proportional hazard regression analysis and stepwise variable selection were conducted to evaluate the contribution of independent prognostic factors associated with patient survivals. The microRNA signature risk-score, age, sex, stage and histology were used as covariates. All analyses were performed using SAS version 9.1 software (SAS Institute Inc). Two-tailed tests and P values <0.05 indicates that results are statistically significant.

More details of performing the methods described above can be found in Yu et al., Cancer Cell 13, 48-57 (2008).

Results (a) Identification and Verification of a MicroRNA Signature for Predicting the Overall Survival and Relapse-Free Survival of NSCLC Patients Table 1 below shows the clinical characteristics of the 56 NSCLC patients assigned to the training dataset and the 56 NSCLC patients assigned to the testing dataset. There was no significant difference between patients in these two datasets with respect to their clinical characteristics.

The expression levels of microRNAs were determined in all of these patients following the method described above. Results obtained from the training dataset were subjected to univariate Cox regression analysis to identify the microRNAs whose expression levels were associated with post-treatment death/survival. Five microRNAs, i.e., hsa-miR137, hsa-miR372, hsa-miR182*, hsa-miR221, and hsa-let-7a, were found to be associated with overall survival of the patients in the training dataset. Among them, the former three are high-risk microRNAs and the latter two are protective microRNAs.

Based on the expression levels of these five microRNAs, a patient's risk score was calculated following the formula: (0.15×expression level of hsa-miR-137)+(0.31× expression level of hsa-miR-372)+(0.28×expression level of hsa-miR182*)+(−0.13× expression level of hsa-miR-221)+(−0.14×expression level of hsa-let-7a). Patients having a risk score higher than −7.1 were assigned to a high-risk group and patients having a risk score lower than −7.1 were assigned to a low-risk group.

TABLE 1

Clinicopathologic Characteristics of 112 NSCLC Patients

| Characteristic | Training dataset No. of patients (%) n = 56 | Testing dataset No. of patients (%) n = 56 | P value |
|---|---|---|---|
| Age (mean ± SD) | 66.5 ± 10.0 | 65.3 ± 14.1 | 0.606[†] |
| Gender | | | |
| Male | 45 (80) | 43 (77) | 0.818[‡] |
| Female | 11 (20) | 13 (23) | |
| Stage | | | |
| I | 21 (38) | 26 (46) | 0.549[‡] |
| II | 14 (25) | 14 (25) | |
| III | 21 (37) | 16 (29) | |
| Cell type | | | |
| Adenocarcinoma | 25 (45) | 30 (53) | 0.150[‡] |
| Squamous cell carcinoma | 25 (45) | 25 (45) | |
| Others | 6 (10) | 1 (2) | |

[†]t test.
[‡]Fisher's exact test.

The clinical characteristics of the patients in both high-risk and low-risk groups are summarized in Table 2 below.

TABLE 2

Clinical Characteristics of NSCLC Patients in Both The High-Risk and Low-Risk Datasets

| Characteristic | Patients in high-risk group | Patients in low-risk group | P value |
|---|---|---|---|
| Training dataset (n = 56) | n = 28 | n = 28 | |
| Age (mean ± SD) | 65.7 ± 10.3 | 67.3 ± 9.7 | 0.549[†] |
| Gender | | | |
| Male | 21 (75) | 24 (86) | 0.503[‡] |
| Female | 7 (25) | 4 (14) | |
| Stage | | | |
| I | 5 (18) | 16 (57) | 0.008[‡] |
| II | 8 (28) | 6 (22) | |
| III | 15 (54) | 6 (21) | |
| Cell type | | | |
| Adenocarcinoma | 15 (54) | 10 (36) | 0.353[‡] |
| Squamous cell carcinoma | 10 (36) | 15 (54) | |
| Others | 3 (10) | 3 (10) | |
| Testing dataset (n = 56) | n = 26 | n = 30 | |
| Age (mean ± SD) | 66.5 ± 13.6 | 64.3 ± 14.7 | 0.57[†] |
| Gender | | | |
| Male | 22 (85) | 21 (70) | 0.224[‡] |
| Female | 4 (15) | 9 (30) | |
| Stage | | | |
| I | 11 (42) | 15 (50) | 0.340[‡] |
| II | 5 (19) | 9 (30) | |
| III | 10 (39) | 6 (20) | |
| Cell type | | | |
| Adenocarcinoma | 17 (65) | 13 (43) | 0.179[‡] |
| Squamous cell carcinoma | 9 (35) | 16 (53) | |
| Others | 0 (0) | 1 (4) | |
| Independent cohort (n = 62) | n = 40 | n = 22 | |
| Age (mean ± SD) | 62.9 ± 10.3 | 64.1 ± 9.1 | 0.634[†] |
| Gender | | | |
| Male | 32 (80) | 10 (45) | 0.010[‡] |
| Female | 8 (20) | 12 (55) | |
| Stage | | | |
| I | 15 (37) | 13 (59) | 0.152[‡] |
| II | 6 (15) | 4 (18) | |
| III | 19 (48) | 5 (23) | |
| Cell type | | | |
| Adenocarcinoma | 21 (52) | 9 (41) | 0.563[‡] |
| Squamous cell carcinoma | 13 (33) | 8 (36) | |
| Others | 6 (15) | 5 (23) | |

[†] t test.
[‡] Fisher's exact test.

FIG. 1 shows the risk stores, survival status, and microRNA expression profiles of the NSCLC patients in both the training and testing datasets. Patients having high risk scores express high levels of any of the three high-risk microRNAs and low levels of any of the two protective microRNAs. To the contrary, patients having low risk stores express low levels of any of the high-risk microRNAs and high levels of any of the protective microRNAs.

In the training dataset, the patients in the high-risk group showed shorter post-survival periods than those in the low-risk group. See FIG. 2, Panel A. The median overall survival period of patients in the high-risk group was about 20 month, while that of patients in the low-risk group was longer than 50 months. As to the median relapse-free survival period, it was about 10 month in the high-risk group and longer than 45 months in the low-risk group. See FIG. 2, Panel A. These results indicate that the expression pattern of the five microRNAs mentioned above (i.e., a microRNA signature), based on which a patient is assigned either to the high-risk or the low-risk group, is associated with a cancer patient's post-treatment survival period.

The just-mentioned association between the microRNA signature and survival prospect was verified in the testing dataset. Similar to the results obtained from the training dataset, results obtained from the testing dataset also showed that the patients in the low-risk group lived much longer after treatment than the patients in the high-risk group. See FIG. 2, Panel B. In the high-risk group, the median overall survival period was about 25 month, and the median relapse-free survival period was about 14 month. In the low-risk group, the median overall survival period and relapse-free survival period were longer than 50 months and longer than 40 month, respectively. All these results were statistically significant.

Multivariate Cox regression analysis showed that, among the factors listed in Table 3 below, this microRNA signature was the only factor associated with the overall survival (hazard ratio [HR]=10.31, P=0.002) in NSCLC patients.

TABLE 3

Multivariate Cox Regression* Analysis of The MicroRNA Signature and Survivals in NSCLC Patients

| Variable | Hazard ratio | 95% CI | P value |
|---|---|---|---|
| Overall survival | | | |
| Training dataset (n = 56) | | | |
| microRNA expression signature | 10.31 | 2.33 to 45.56 | 0.002 |
| Testing dataset (n = 56) | | | |
| microRNA expression signature | 3.65 | 1.29 to 10.37 | 0.015 |
| Stage | 8.12 | 2.83 to 23.25 | <0.001 |
| Age | 1.08 | 1.03 to 1.14 | 0.002 |
| Independent cohort (n = 62) | | | |
| microRNA expression signature | 2.81 | 1.13 to 7.01 | 0.026 |
| Stage | 2.35 | 1.13 to 4.89 | 0.022 |
| Relapse-free survival | | | |
| Training dataset (n = 56) | | | |
| microRNA expression signature | 3.29 | 1.24 to 8.71 | 0.016 |
| Stage | 2.63 | 1.10 to 6.25 | 0.029 |
| Testing dataset (n = 56) | | | |
| microRNA expression signature | 2.86 | 1.20 to 6.82 | 0.018 |
| Stage | 2.97 | 1.32 to 6.69 | 0.009 |
| Independent cohort (n = 62) | | | |
| microRNA expression signature | 2.39 | 1.12 to 5.10 | 0.024 |
| Stage | 2.76 | 1.43 to 5.34 | 0.003 |
| Age | 0.93 | 0.90 to 0.97 | <0.001 |

*Variables were selected through stepwise selection method (b) Validation of the microRNA Signature for Survival Prediction in an Independent Cohort The microRNA signature mentioned above was validated for its use in predicting post-treatment survival prospect in an independent cohort, including 62 NSCLC patients.

Figure 2:
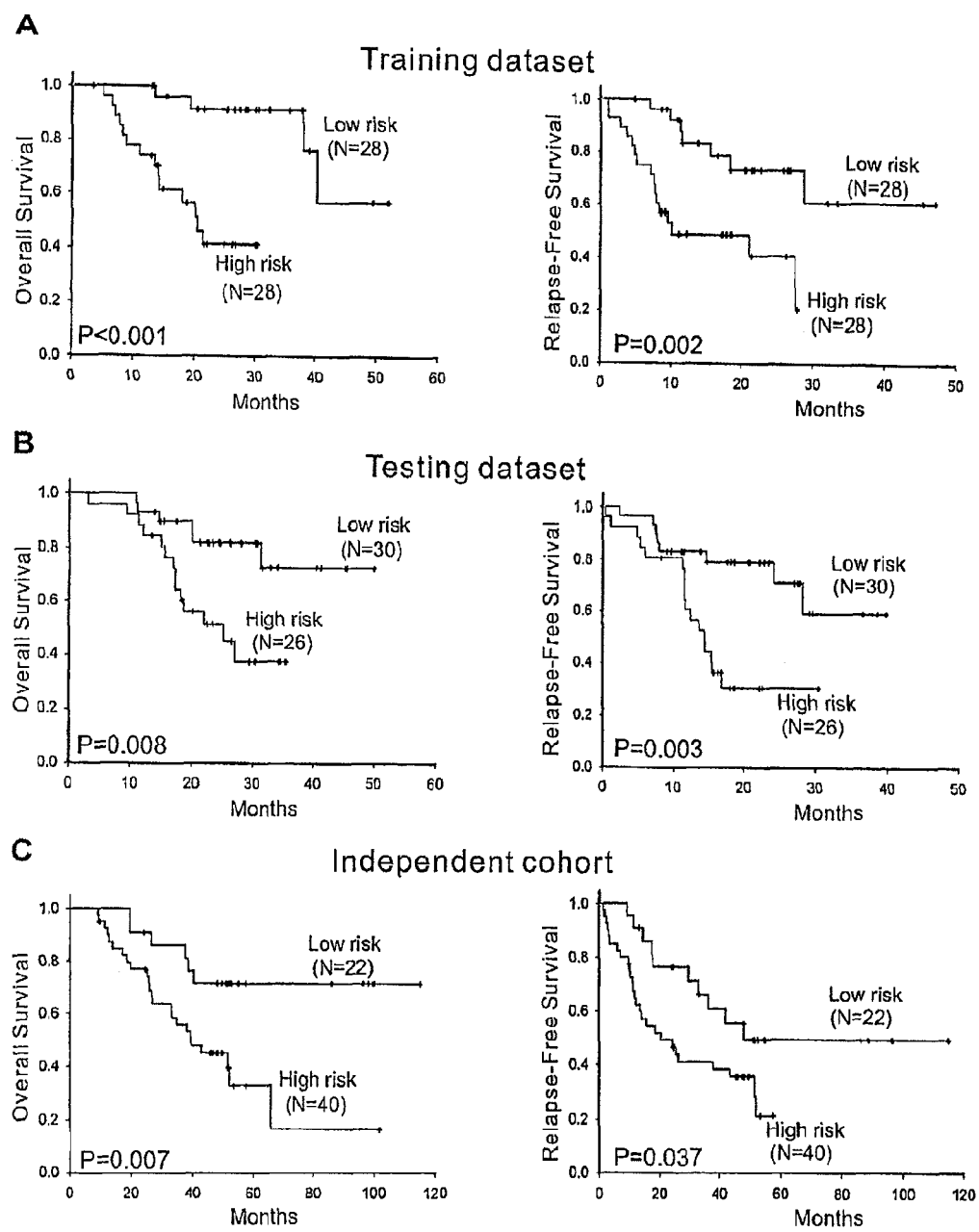
FIG. 2 is a diagram showing Kaplan-Meier estimates of the overall survival and relapse-free survival of the NSCLC patients in both low-risk and high-risk groups. Panel A shows results obtained from 56 patients in a training dataset; Panel B shows results obtained from 56 patients in a testing dataset; and Panel C shows results obtained from 62 patients in an independent cohort.

The clinical characteristics of the 62 patients are summarized in Table 2 above. The risk score of each patient was calculated based on his or her expression patterns of the five microRNAs following the method described above. The patients having risk scores higher than −7.1 were assigned to a high-risk group and the patients having risk scores below −7.1 were assigned to a low-risk group. As shown in FIG. 2, Panel C, the patients in the high-risk group had shorter post-treatment survival periods than those in the low-risk group, i.e., 40 months versus longer than 120 months in terms of median overall survival period and 20 months versus 48 months in terms of median relapse-free survival period. See FIG. 2C. Multivariate Cox regression analysis showed that microRNA signature and stage were associated with overall survival and relapse-free survival (see Table 3 supra).

These results confirm that the microRNA signature can be used in predicting a cancer patient's post-treatment survival prospect.

Figure 3:
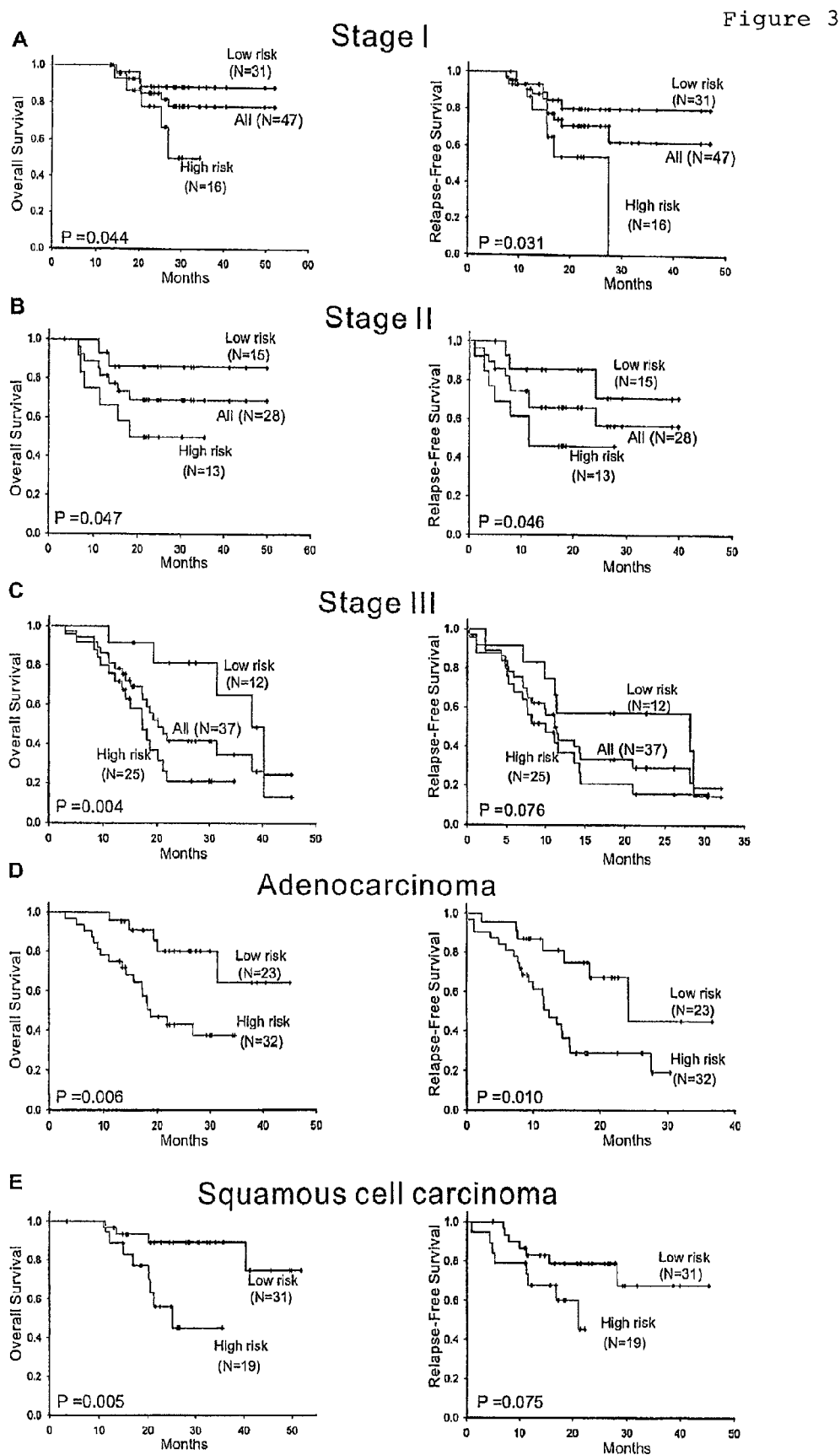
FIG. 3 is a diagram showing Kaplan-Meier estimates of the overall survival and relapse-free survival of NSCLC patients in both low-risk and high-risk groups. Panel A shows results obtained from state I NSCLC patients (n=47); Panel B shows results obtained from stage II NSCLC patients (n=28); Panel C shows results obtained from stage III NSCLC patients (n=37); Panel D shows results obtained from adenocarcinoma patients (n=55); and Panel E shows results obtained from squamous cell carcinoma patients (n=50).

(c) Association between the MicroRNA Signature and Post-Treatment Survival of NSCLC Patients in Different Disease Stages and Histological Subgroups NSCLC patients in different disease stages and in different histological subgroups were assigned to high-risk and low-risk groups based on their microRNA signature following the method described above. As shown in FIG. 3, the patients in the low-risk groups lived longer after treatment than the patients in the high-risk groups. See Panels A-E. These results indicate that the microRNA signature can also be used to predict the post-treatment survival prospect for NSCLC patients in different disease stages, i.e., stage I, II or III, and in different histological sub-groups, i.e., adenocarcinoma or squamous cell carcinoma sub-groups.

(d) MicroRNA Signatures as Predictors of Patient Survival in NSCLC

Univariate Cox regression analysis showed that the expression level of each of the 5 microRNAs, i.e., hsa-miR137, hsa-miR372, hsa-miR182*, hsa-miR221, or hsa-let-7a, was associated with NSCLC survival. See Table 4 below. The log-rank analysis showed that the microRNA signature composed of all of the five microRNAs is the optimal predictor for patient survival. See also Table 4 below.

In addition, univariate Cox regression analysis showed that a microRNA signature composed of any four of the aforementioned five microRNAs was also associated with patient post-treatment survival. See Table 5 below.

TABLE 4

The P values of log-rank test in Kaplan-Meier survival analysis of the 5-microRNA signature compared to individual microRNA expression in NSCLC patients

| microRNA* | Training dataset | Testing dataset | Independent cohort |
|---|---|---|---|
| | Overall survival | | |
| All five microRNAs | <0.001 | 0.008 | 0.007 |
| hsa-miR-221 | 0.021 | 0.264 | 0.955 |
| hsa-let-7a | 0.906 | 0.292 | 0.356 |
| hsa-miR-137 | 0.026 | 0.347 | 0.005 |
| hsa-miR-372 | 0.358 | 0.011 | <0.001 |
| hsa-miR-182* | 0.126 | 0.005 | 0.904 |
| | Relapse-free survival | | |
| All five microRNAs | 0.002 | 0.003 | 0.037 |
| hsa-miR-221 | 0.008 | 0.680 | 0.751 |
| hsa-let-7a | 0.258 | 0.225 | 0.461 |
| hsa-miR-137 | 0.086 | 0.619 | 0.007 |
| hsa-miR-372 | 0.615 | 0.005 | 0.003 |
| hsa-miR-182* | 0.343 | 0.005 | 0.961 |

*two groups were separated based on median

TABLE 5

The P values of Log-Rank Test in Kaplan-Meier Survival Analysis of The 5-microRNA Signature Versus 4-microRNA Signatures in NSCLC Patients

|  | Training dataset | Testing dataset | Independent cohort |
|---|---|---|---|
| *Overall survival* | | | |
| All five microRNAs | <0.001 | 0.008 | 0.007 |
| Four of the five microRNAs | | | |
| hsa-miR137, hsa-miR372, hsa-miR182*, and hsa-let-7a | <0.001 | 0.007 | 0.022 |
| hsa-miR137, hsa-miR372, hsa-miR182*, and hsa-miR221 | 0.001 | 0.006 | 0.057 |
| hsa-miR372, hsa-miR182*, hsa-miR221, and hsa-let-7a | 0.020 | 0.038 | 0.058 |
| hsa-miR137, hsa-miR182*, hsa-miR221, and hsa-let-7a | 0.022 | 0.141 | 0.100 |
| hsa-miR137, hsa-miR372, hsa-miR221, or hsa-let-7a | <0.001 | 0.204 | 0.003 |
| *Relapse-free survival* | | | |
| All five microRNAs | 0.002 | 0.003 | 0.037 |
| Four of the five microRNAs | | | |
| hsa-miR137, hsa-miR372, hsa-miR182*, and hsa-let-7a | 0.012 | 0.013 | 0.078 |
| hsa-miR137, hsa-miR372, hsa-miR182*, and hsa-miR221 | 0.033 | 0.008 | 0.154 |
| hsa-miR372, hsa-miR182*, hsa-miR221, and hsa-let-7a | 0.139 | 0.006 | 0.189 |
| hsa-miR137, hsa-miR182*, hsa-miR221, and hsa-let-7a | 0.037 | 0.441 | 0.116 |
| hsa-miR137, hsa-miR372, hsa-miR221, or hsa-let-7a | <0.001 | 0.048 | 0.015 |

(e) Putative Gene Targets of microRNAs

GeneSpring pathway annotated software (Silicon Genetics) was applied to predict the putative pathways that the five microRNAs might be involved and the results thus obtained are summarized in Tables 6 and 7 below.

TABLE 6

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| let-7a | ABCB9 | Hs.511951 | 4 | ABC transporters - General 02010 | GO: 6857<br>GO: 15031<br>GO: 7283 | GO: 5524<br>GO: 16887<br>GO: 42626<br>GO: 166<br>GO: 15198<br>GO: 5215 | GO: 43190<br>GO: 5783<br>GO: 16021<br>GO: 5764 |
| let-7a | ABCC10 | Hs.55879 | 4 | ABC transporters - General 02010 | GO: 6810 | GO: 5524<br>GO: 16887<br>GO: 42626<br>GO: 166 | GO: 16021 |
| let-7a | ABCC5 | Hs.368563 | 4 | ABC transporters - General 02010 | GO: 6810 | GO: 5524<br>GO: 16887<br>GO: 42626<br>GO: 15239<br>GO: 166<br>GO: 8514 | GO: 16021<br>GO: 5887<br>GO: 5624 |
| let-7a | ATP2A2 | Hs.506759 | 4 | Calcium signaling pathway 04020 | GO: 6816<br>GO: 6812<br>GO: 7155<br>GO: 8544<br>GO: 8152<br>GO: 15992 | GO: 5524<br>GO: 48155<br>GO: 5509<br>GO: 5388<br>GO: 16787<br>GO: 16820<br>GO: 287 GO: 166 | GO: 5887<br>GO: 16020<br>GO: 5624<br>GO: 5792<br>GO: 16529 |
| let-7a | BZW1 | Hs.355983 | 4 | | GO: 6446 | GO: 3743 | |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| let-7a | CDC25A | Hs.1634 | 4 | Cell cycle 04110; Cell Cycle 69278; Cell Cycle Checkpoints 69620 | GO: 51301<br>GO: 8283<br>GO: 7067<br>GO: 6470<br>GO: 79 | GO: 16787<br>GO: 4725 | GO: 8372<br>GO: 5622 |
| let-7a | CHD4 | Hs.162233 | 4 | | GO: 6333<br>GO: 16568<br>GO: 7001)<br>GO: 6357<br>GO: 6350 | GO: 5524<br>GO: 4003<br>GO: 3677<br>GO: 3682<br>GO: 16787<br>GO: 46872<br>GO: 166<br>GO: 5515<br>GO: 8270 | GO: 785<br>GO: 5634 |
| let-7a | CHD9 | Hs.59159 | 4 | | GO: 6333 | GO: 5524<br>GO: 3677<br>GO: 3682<br>GO: 4386 | GO: 785<br>GO: 16021<br>GO: 5634 |
| let-7a | CHRD | Hs.166186 | 4 | TGF-beta signaling pathway 04350 | GO: 7275<br>GO: 1501 | GO: 5554 | GO: 8372 |
| let-7a | DHX57 | Hs.468226 | 4 | | | | |
| let-7a | DTX2 | Hs.187058 | 4 | Notch signaling pathway 04330 | GO: 7219<br>GO: 16567 | GO: 46872<br>GO: 4842<br>GO: 8270 | GO: 5634<br>GO: 151 |
| let-7a | E2F5 | Hs.445758 | 4 | Cell cycle 04110; TGF-beta signaling pathway 04350; Cell Cycle 69278 | GO: 74 GO: 6355<br>GO: 6350 | GO: 5515<br>GO: 3700 | GO: 5634<br>GO: 5667 |
| let-7a | EZH2 | Hs.444082 | 4 | | GO: 6325<br>GO: 6355<br>GO: 6350 | GO: 3677 | GO: 5634 |
| let-7a | FASLG | Hs.2007 | 4 | Apoptosis 04210; Cytokine-cytokine receptor interaction 04060; MAPK signaling pathway 04010; Natural killer cell mediated cytotoxicity 04650; Type I diabetes mellitus 04940; Apoptosis 109581 | GO: 6915<br>GO: 7267<br>GO: 6955<br>GO: 6917<br>GO: 43123<br>GO: 7165 | GO: 5164 | GO: 5615<br>GO: 5887<br>GO: 16020 |
| let-7a | GALE | Hs.557524 | 4 | Galactose metabolism 00052; Nucleotide sugars metabolism 00520; Metabolism of sugars 71387 | GO: 5975<br>GO: 6012<br>GO: 9225 | GO: 51287<br>GO: 3978<br>GO: 3824<br>GO: 16853 | |
| let-7a | GIPC1 | Hs.6454 | 4 | mRNA processing | GO: 7186 | GO: 5515<br>GO: 5102 | GO: 5829<br>GO: 16020<br>GO: 5624<br>GO: 5625 |
| let-7a | GOLT1B | Hs.62275 | 4 | | GO: 43123<br>GO: 16192 | GO: 4871 | GO: 16021 |
| let-7a | HOXC11 | Hs.127562 | 4 | | GO: 7275<br>GO: 7492<br>GO: 6355 | GO: 3702<br>GO: 3700 | GO: 5634 |
| let-7a | IDH2 | Hs.513141 | 4 | Krebs-TCA Cycle; Citrate cycle; Glutathione metabolism; Reductive carboxylate cycle | | | |
| let-7a | JMJD1A | Hs.531819 | 4 | | | | |
| let-7a | LOC151579 | Hs.529231 | 4 | | | | |
| let-7a | LRIG3 | Hs.253736 | 4 | | | | |
| let-7a | MAP4K3 | Hs.468239 | 4 | MAPK signaling pathway 04010 | GO: 7254<br>GO: 6468<br>GO: 7243<br>GO: 6950 | GO: 5524<br>GO: 166<br>GO: 4674<br>GO: 5083<br>GO: 16740 | |
| let-7a | MESDC1 | Hs.513071 | 4 | | | | |
| let-7a | MLL5 | Hs.567540 | 4 | | GO: 6355 | GO: 5515<br>GO: 8270 | |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| let-7a | NDST2 | Hs.225129 | 4 | Chondroitin/Heparan sulfate biosynthesis 00532 | | GO: 8146 GO: 16740 | GO: 5795 GO: 16021 |
| let-7a | NID2 | Hs.369840 | 4 | | GO: 7155 GO: 7160 | GO: 5509 GO: 5518 | GO: 5604 GO: 16020 |
| let-7a | PBX3 | Hs.428027 | 4 | | GO: 7387 GO: 9790 GO: 30902 GO: 7388 GO: 6355 GO: 45898 | GO: 5515 GO: 3700 | GO: 5634 |
| let-7a | RANBP2 | Hs.199561 | 4 | | GO: 46907 GO: 6457 GO: 6606 | GO: 8536 GO: 5488 GO: 16853 GO: 46872 GO: 3755 GO: 8270 | GO: 5643 GO: 5634 |
| let-7a | RFXDC1 | Hs.352276 | 4 | | GO: 6355 GO: 6388 GO: 6350 | GO: 3677 GO: 213 | GO: 214 |
| let-7a | SEMA4C | Hs.516220 | 4 | Axon guidance 04360 | GO: 30154 GO: 7399 | GO: 4872 | GO: 16021 GO: 16020 |
| let-7a | SLC20A1 | Hs.187946 | 4 | | | | |
| let-7a | SLC35D2 | Hs.494556 | 4 | | GO: 4 | GO: 5338 | GO: 8372 |
| let-7a | SOCS1 | Hs.50640 | 4 | Insulin signaling pathway 04910; Jak-STAT signaling pathway 04630; Type II diabetes mellitus 04930 | GO: 7259 GO: 7242 GO: 46426 GO: 1558 GO: 6512 | GO: 5159 GO: 19901 GO: 4860 | GO: 5737 |
| let-7a | STXBP5 | Hs.93534 | 4 | | | | |
| let-7a | TMEM2 | Hs.494146 | 4 | | | | GO: 16021 |
| let-7a | TRAPPC1 | Hs.24379 | 4 | | | | |
| let-7a | TSCOT | Hs.512668 | 4 | | | | |
| let-7a | TUSC2 | Hs.517981 | 4 | | | | |
| let-7a | UHRF2 | Hs.493401 | 4 | | | | |
| let-7a | USP21 | Hs.8015 | 4 | | GO: 6512 GO: 6511 | GO: 4197 GO: 8233 GO: 5515 GO: 4221 | GO: 8372 |
| let-7a | USP32 | Hs.132868 | 4 | | GO: 6512 GO: 6511 | GO: 5509 GO: 4197 GO: 4221 | |
| let-7a | ACTA1 | Hs.1288 | 3 | Smooth muscle contraction; Striated muscle contraction | GO: 7517 GO: 30240 | GO: 43531 GO: 5524 GO: 3774 GO: 17022 GO: 166 GO: 5515 GO: 5200 | GO: 5884 GO: 5856 GO: 1725 GO: 5865 |
| let-7a | ACVR1B | Hs.438918 | 3 | Adherens junction 04520; Cytokine-cytokine receptor interaction 04060; MAPK signaling pathway 04010; TGF-beta signaling pathway 04350 | GO: 6468 GO: 7178 | GO: 5524 GO: 287 GO: 30145 GO: 166 GO: 4674 GO: 4872 GO: 16740 GO: 5024 | GO: 5887 GO: 16020 |
| let-7a | ADAM15 | Hs.312098 | 3 | | GO: 7155 GO: 7160 GO: 6508 | GO: 17124 GO: 46872 GO: 4222 GO: 5515 GO: 8270 | GO: 16021 |
| let-7a | ADRB2 | Hs.2551 | 3 | Calcium signaling pathway 04020; Neuroactive ligand-receptor interaction 04080 | GO: 7186 GO: 7188 GO: 187 GO: 7190 GO: 8333 GO: 7243 GO: 6898 GO: 7171) | GO: 4941 GO: 5515 GO: 4872 GO: 1584 | GO: 5768 GO: 5887 GO: 5764 GO: 5886 |
| let-7a | ANKFY1 | Hs.513875 | 3 | | GO: 6897 | GO: 46872 GO: 5515 GO: 8270 | GO: 10008 GO: 16020 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| let-7a | ANKRD43 | Hs.13308 | 3 | | | | |
| let-7a | AP1S1 | Hs.489365 | 3 | | GO: 6886<br>GO: 6898 | GO: 5515<br>GO: 8565 | GO: 30121<br>GO: 5795<br>GO: 5802<br>GO: 5905 |
| let-7a | APBB3 | Hs.529449 | 3 | | | GO: 5515 | GO: 5737 |
| let-7a | ARHGAP20 | Hs.6136 | 3 | | | | |
| let-7a | ARL5 | Hs.470233 | 3 | | GO: 6886<br>GO: 7264 | GO: 5525<br>GO: 166 | |
| let-7a | ARMC8 | Hs.266826 | 3 | | | | |
| let-7a | ATXN1 | Hs.434961 | 3 | | | GO: 3723 | GO: 5737<br>GO: 5634 |
| let-7a | B3GNT6 | Hs.8526 | 3 | Blood group glycolipid biosynthesis-neolactoseries 00602; Keratan sulfate biosynthesis 00533 | GO: 30311 | GO: 8532<br>GO: 16757 | GO: 5795<br>GO: 30173<br>GO: 16021 |
| let-7a | BCL2L1 | Hs.516966 | 3 | Amyotrophic lateral sclerosis 05030; Apoptosis 04210; Jak-STAT signaling pathway 04630; Neurodegenerative Disorders 01510; Apoptosis 109581 | GO: 6916<br>GO: 8637<br>GO: 8634<br>GO: 42981 | GO: 42802 | GO: 16021<br>GO: 16020<br>GO: 5741<br>GO: 5739 |
| let-7a | BNC2 | Hs.435309 | 3 | | GO: 6355<br>GO: 6350 | GO: 46872<br>GO: 3676<br>GO: 8270 | GO: 5634 |
| let-7a | BRD3 | Hs.522472 | 3 | | GO: 4 | GO: 5554 | GO: 5634 |
| let-7a | BTBD3 | Hs.244590 | 3 | | | GO: 5515 | |
| let-7a | BTG2 | Hs.519162 | 3 | | GO: 6281<br>GO: 8285<br>GO: 6355<br>GO: 6350 | GO: 3700 | |
| let-7a | BZW2 | Hs.487635 | 3 | | | | |
| let-7a | C1orf22 | Hs.523811 | 3 | Aminosugars metabolism 00530; Glycosaminoglycan degradation 00531; Nucleotide sugars metabolism 00520 | GO: 5975<br>GO: 6487<br>GO: 6508 | GO: 5509<br>GO: 16798<br>GO: 4571<br>GO: 8233 | GO: 5783<br>GO: 16020 |
| let-7a | CALU | Hs.7753 | 3 | | GO: 4 | GO: 5509 | GO: 5794<br>GO: 5783 |
| let-7a | CAP1 | Hs.370581 | 3 | | GO: 7190<br>GO: 7163<br>GO: 7165 | GO: 3779 | GO: 16020 |
| let-7a | CASKIN1 | Hs.530863 | 3 | | GO: 7165 | GO: 5515 | GO: 5737 |
| let-7a | CDC34 | Hs.514997 | 3 | Ubiquitin mediated proteolysis | | | |
| let-7a | CDYL | Hs.269092 | 3 | | GO: 6333<br>GO: 8152<br>GO: 7283 | GO: 3824<br>GO: 3682<br>GO: 8233 | GO: 785<br>GO: 5634 |
| let-7a | COIL | Hs.532795 | 3 | | | | GO: 5634 |
| let-7a | COL15A1 | Hs.409034 | 3 | | GO: 1525<br>GO: 7155<br>GO: 30154<br>GO: 6817 | GO: 5515<br>GO: 5198 | GO: 5582<br>GO: 5737<br>GO: 5578) |
| let-7a | COL1A1 | Hs.172928 | 3 | Cell Communication 01430; ECM-receptor interaction 04512; Focal adhesion 04510; Hemostasis 109582 | GO: 8544<br>GO: 6817<br>GO: 7605<br>GO: 1501 | GO: 5201<br>GO: 8147 | GO: 5581<br>GO: 5584<br>GO: 5737 |
| let-7a | COL1A2 | Hs.489142 | 3 | Cell Communication 01430; ECM-receptor interaction 04512; Focal adhesion 04510; Hemostasis 109582 | GO: 4 GO: 6817<br>GO: 7605<br>GO: 1501<br>GO: 7169 | GO: 5201<br>GO: 8147 | GO: 5581<br>GO: 5584<br>GO: 5737 |
| let-7a | COL24A1 | Hs.47312 | 3 | | | | |
| let-7a | COL3A1 | Hs.443625 | 3 | Inflammatory Response Pathway | | | |
| let-7a | COL4A1 | Hs.17441 | 3 | | GO: 6817 | GO: 5201 | GO: 5581<br>GO: 5587<br>GO: 5737 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| let-7a | COL4A2 | Hs.508716 | 3 | | | | |
| let-7a | COL4A5 | Hs.369089 | 3 | | | | |
| let-7a | CPA4 | Hs.93764 | 3 | | GO: 16573<br>GO: 6508 | GO: 4182<br>GO: 4180<br>GO: 46872<br>GO: 8237<br>GO: 8270 | GO: 8372 |
| let-7a | CPD | Hs.446079 | 3 | | GO: 6508 | GO: 4182<br>GO: 4187<br>GO: 4180<br>GO: 46872<br>GO: 8472<br>GO: 8237<br>GO: 8270 | GO: 16021<br>GO: 5624 |
| let-7a | CPEB2 | Hs.374216 | 3 | | | | |
| let-7a | CPEB3 | Hs.131683 | 3 | | | GO: 3676<br>GO: 166 | |
| let-7a | CPEB4 | Hs.127126 | 3 | | | | |
| let-7a | CPM | Hs.434948 | 3 | | | | |
| let-7a | CPSF4 | Hs.489287 | 3 | mRNA processing | GO: 6397 | GO: 3723<br>GO: 46872<br>GO: 8270 | GO: 5634 |
| let-7a | CTNS | Hs.187667 | 3 | | GO: 15811<br>GO: 6520<br>GO: 6810 | GO: 15184 | GO: 16021<br>GO: 5765 |
| let-7a | CYP46A1 | Hs.25121 | 3 | | GO: 6707<br>GO: 6118<br>GO: 6629<br>GO: 7399<br>GO: 8202 | GO: 20037<br>GO: 5506<br>GO: 46872<br>GO: 8395 | GO: 5783<br>GO: 16021<br>GO: 5792 |
| let-7a | DDEF1 | Hs.106015 | 3 | | GO: 43087 | GO: 5096<br>GO: 46872<br>GO: 5515<br>GO: 8270 | GO: 16020 |
| let-7a | DDX19 | Hs.221761 | 3 | | | | |
| let-7a | DIMT1L | Hs.533222 | 3 | | | | |
| let-7a | DLC1 | Hs.134296 | 3 | | GO: 7010<br>GO: 30308<br>GO: 30155<br>GO: 7165 | GO: 5100<br>GO: 5515 | GO: 5737<br>GO: 5576 |
| let-7a | DMD | Hs.495912 | 3 | Striated muscle contraction | GO: 4 GO: 7016<br>GO: 6936<br>GO: 7517 | GO: 3779<br>GO: 5509<br>GO: 5554<br>GO: 5515<br>GO: 5200<br>GO: 8307<br>GO: 5198<br>GO: 8270 | GO: 8372<br>GO: 5856<br>GO: 16010 |
| let-7a | DMP1 | Hs.128556 | 3 | | GO: 7155<br>GO: 30198<br>GO: 1503 | GO: 5509<br>GO: 5178 | GO: 5578) |
| let-7a | DMTF1 | Hs.558441 | 3 | | | | |
| let-7a | DOT1L | Hs.465554 | 3 | Lysine degradation 00310 | GO: 16568 | GO: 18024<br>GO: 8168<br>GO: 16740 | GO: 5634 |
| let-7a | DPF2 | Hs.13495 | 3 | | GO: 6915<br>GO: 8624<br>GO: 6355<br>GO: 6350 | GO: 46872<br>GO: 3676<br>GO: 5515<br>GO: 8270 | GO: 5634 |
| let-7a | DPP3 | Hs.502914 | 3 | | GO: 6508 | GO: 4177<br>GO: 17039<br>GO: 46872<br>GO: 8237<br>GO: 8270 | GO: 5737 |
| let-7a | DST | Hs.485616 | 3 | | GO: 30036<br>GO: 7155<br>GO: 7050<br>GO: 7010<br>GO: 7229<br>GO: 45104 | GO: 3779<br>GO: 51015<br>GO: 5509<br>GO: 5178<br>GO: 8022<br>GO: 5515<br>GO: 5200 | GO: 5604<br>GO: 5737<br>GO: 16023<br>GO: 5856<br>GO: 5615<br>GO: 30056<br>GO: 5911 |
| let-7a | DUSP1 | Hs.171695 | 3 | ; Calcium signaling pathway; Type I | | | |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| let-7a | DUSP16 | Hs.536535 | 3 | diabetes mellitus;; Calcium signaling pathway MAPK signaling pathway 04010 | GO: 45204 GO: 45209 GO: 188 GO: 6470 | GO: 17017 GO: 16787 | GO: 5737 GO: 5634 |
| let-7a | DUSP9 | Hs.144879 | 3 | MAPK signaling pathway 04010 | GO: 7254 GO: 188 GO: 6470 | GO: 17017 GO: 16787 | GO: 5737 GO: 5634 |
| let-7a | DYRK1A | Hs.368240 | 3 | Benzoate degradation via CoA ligation 00632; Inositol phosphate metabolism 00562; Nicotinate and nicotinamide metabolism 00760; Phosphatidylinositol signaling system 04070 | GO: 7399 GO: 18108 | GO: 5524 GO: 4715 GO: 166 GO: 4674 GO: 16740 | GO: 5634 |
| let-7a | EGR3 | Hs.534313 | 3 | | GO: 7623 GO: 7517 GO: 6355 GO: 6350 | GO: 46872 GO: 3700 GO: 8270 | GO: 5634 |
| let-7a | EIF2C1 | Hs.22867 | 3 | | GO: 6412 GO: 6446 | GO: 5515 GO: 3743 | GO: 5850 |
| let-7a | EIF2C3 | Hs.567761 | 3 | | GO: 6412 | GO: 3743 | |
| let-7a | EIF2C4 | Hs.471492 | 3 | | GO: 6412 | GO: 3743 | |
| let-7a | EPHA3 | Hs.123642 | 3 | Axon guidance 04360 | GO: 6468 GO: 7165 GO: 7169 | GO: 5524 GO: 5003 GO: 166 GO: 4674 GO: 4713 GO: 4872 GO: 16740 | GO: 5887 GO: 16020 |
| let-7a | EPHA4 | Hs.371218 | 3 | Calcium signaling pathway | | | |
| let-7a | ERCC6 | Hs.133444 | 3 | DNA Repair 73894 | GO: 6281 GO: 6355 GO: 7605 GO: 6350 GO: 6366 | GO: 5524 GO: 3677 GO: 3678 GO: 3702 GO: 4386 GO: 16787 GO: 166 GO: 5515 | GO: 5634 |
| let-7a | FARP1 | Hs.567409 | 3 | | GO: 7155 | GO: 8092 GO: 5085 | GO: 5737 GO: 5856 GO: 16020 |
| let-7a | FBXL19 | Hs.152149 | 3 | | GO: 6508 GO: 6355 GO: 6512 | GO: 3677 GO: 46872 GO: 5515 GO: 4842 GO: 8270 | GO: 5737 |
| let-7a | FGF11 | Hs.528468 | 3 | | | | |
| let-7a | FLJ21986 | Hs.189652 | 3 | | | | |
| let-7a | FNDC3A | Hs.508010 | 3 | ECM-receptor interaction 04512 | | | |
| let-7a | FRAS1 | Hs.369448 | 3 | | | | |
| let-7a | GALNT1 | Hs.514806 | 3 | O-Glycan biosynthesis 00512 | GO: 6493 | GO: 5509 GO: 30145 GO: 4653 GO: 5529 GO: 16757 | GO: 5795 GO: 16021 |
| let-7a | GATM | Hs.75335 | 3 | Urea cycle and metabolism of amino groups; Glycine, serine and threonine metabolism; Arginine and proline metabolism | | | |
| let-7a | GGA3 | Hs.87726 | 3 | | GO: 6886 GO: 6461 | GO: 30306 GO: 5515 GO: 8565 | GO: 5795 GO: 5802 GO: 30130 GO: 16020 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| let-7a | GNAL | Hs.136295 | 3 | Calcium signaling pathway 04020 | GO: 7186<br>GO: 7165 | GO: 5525<br>GO: 3924<br>GO: 166<br>GO: 4871 | |
| let-7a | GNG5 | Hs.554749 | 3 | Energy Metabolism 163685 | GO: 7186<br>GO: 7165 | GO: 4871 | GO: 5834 |
| let-7a | GNPTAB | Hs.46850 | 3 | | | | |
| let-7a | GRIK2 | Hs.98262 | 3 | Neuroactive ligand-receptor interaction 04080 | GO: 7215<br>GO: 6811<br>GO: 6813<br>GO: 7268<br>GO: 6810 | GO: 5234<br>GO: 5216<br>GO: 4970<br>GO: 15277<br>GO: 5267<br>GO: 4872<br>GO: 5215 | GO: 5887<br>GO: 16020<br>GO: 45211 |
| let-7a | HAND1 | Hs.152531 | 3 | | GO: 7275<br>GO: 7507<br>GO: 6355<br>GO: 6366 | GO: 3700 | GO: 5634 |
| let-7a | HAS2 | Hs.159226 | 3 | | | GO: 50501<br>GO: 16757 | GO: 5887 |
| let-7a | HDHD1A | Hs.185910 | 3 | | GO: 4 GO: 8152 | GO: 3824<br>GO: 5554 | GO: 8372 |
| let-7a | HECTD2 | Hs.535293 | 3 | | GO: 15671<br>GO: 6512 | GO: 20037<br>GO: 5344<br>GO: 4842 | GO: 5622 |
| let-7a | HIC2 | Hs.517434 | 3 | | GO: 45892<br>GO: 6350 | GO: 3677<br>GO: 46872<br>GO: 8022<br>GO: 8270 | GO: 5634 |
| let-7a | HOMER2 | Hs.459142 | 3 | | GO: 7216 | | |
| let-7a | HOXA9 | Hs.127428 | 3 | | GO: 4 GO: 7275<br>GO: 6355 | GO: 5554<br>GO: 3700<br>GO: 16563 | GO: 5634 |
| let-7a | HOXB4 | Hs.532669 | 3 | | GO: 7275<br>GO: 6355 | GO: 3700 | GO: 5634 |
| let-7a | HOXD1 | Hs.83465 | 3 | | GO: 7275<br>GO: 6355 | GO: 3700 | GO: 5634 |
| let-7a | HTR4 | Hs.483773 | 3 | Calcium signaling pathway 04020; Neuroactive ligand-receptor interaction 04080 | GO: 7187<br>GO: 7165 | GO: 4935<br>GO: 4872<br>GO: 1584<br>GO: 4993 | GO: 5887 |
| let-7a | IL13 | Hs.845 | 3 | Cytokine-cytokine receptor interaction 04060; Jak-STAT signaling pathway 04630 | GO: 19735)<br>GO: 6928<br>GO: 8283<br>GO: 7267<br>GO: 6954<br>GO: 7165 | GO: 8009<br>GO: 5144<br>GO: 4871 | GO: 5615<br>GO: 5625 |
| let-7a | INPP5A | Hs.523360 | 3 | Inositol phosphate metabolism 00562; Phosphatidylinositol signaling system 04070 | GO: 7154 | GO: 16787<br>GO: 4437<br>GO: 4445 | GO: 16020 |
| let-7a | IRS2 | Hs.442344 | 3 | Adipocytokine signaling pathway 04920; Insulin signaling pathway 04910; Type II diabetes mellitus 04930; Insulin receptor mediated signalling 74752 | GO: 6006<br>GO: 8284<br>GO: 7165 | GO: 5158<br>GO: 4871 | |
| let-7a | ITGB3 | Hs.218040 | 3 | ECM-receptor interaction 04512; Focal adhesion 04510; Hematopoietic cell lineage 04640; Regulation of actin cytoskeleton 04810; Hemostasis 109582 | GO: 7596<br>GO: 7155<br>GO: 7160<br>GO: 7275<br>GO: 7229 | GO: 42802<br>GO: 4872 | GO: 8305 |
| let-7a | KCNC2 | Hs.27214 | 3 | | | | |
| let-7a | KIF1B | Hs.97858 | 3 | | GO: 8089<br>GO: 9790<br>GO: 7018<br>GO: 7270<br>GO: 7274 | GO: 5524<br>GO: 16887<br>GO: 19894<br>GO: 8017<br>GO: 3777 | GO: 30659<br>GO: 5874<br>GO: 5875<br>GO: 5739 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| let-7a | KIF2 | Hs.558351 | 3 | | GO: 7018 | GO: 166<br>GO: 5515<br>GO: 5524<br>GO: 3777<br>GO: 166 | GO: 5856<br>GO: 5874<br>GO: 5875 |
| let-7a | KLF9 | Hs.150557 | 3 | Circadian Exercise | GO: 6357<br>GO: 6350 | GO: 46872<br>GO: 3700<br>GO: 8270 | GO: 5634 |
| let-7a | KPNA4 | Hs.288193 | 3 | | GO: 6607<br>GO: 6886 | GO: 5488<br>GO: 8565 | GO: 5634 |
| let-7a | LOC283859 | Hs.298434 | 3 | Wnt signaling pathway 04310 | | | |
| let-7a | LOC643176 | Hs.403917 | 3 | | | | |
| let-7a | LOXL3 | Hs.469045 | 3 | | | | |
| let-7a | LOXL4 | Hs.306814 | 3 | Arginine and proline metabolism 00330 | | GO: 5507<br>GO: 46872<br>GO: 16491<br>GO: 4720<br>GO: 5044 | GO: 16020 |
| let-7a | LRIG1 | Hs.518055 | 3 | | | | |
| let-7a | LRIG2 | Hs.448972 | 3 | | | | |
| let-7a | MAP3K7IP2 | Hs.269775 | 3 | MAPK signaling pathway 04010; Toll-like receptor signaling pathway 04620 | | | |
| let-7a | MED6 | Hs.497353 | 3 | MED6 | GO: 45944 | GO: 3702<br>GO: 4872<br>GO: 3713 | GO: 119<br>GO: 5634 |
| let-7a | MEF2D | Hs.314327 | 3 | | GO: 7517<br>GO: 6355<br>GO: 6350<br>GO: 6366 | GO: 3713<br>GO: 3700 | GO: 5634 |
| let-7a | MEIS2 | Hs.510989 | 3 | | GO: 122<br>GO: 6355 | GO: 3704<br>GO: 3714<br>GO: 3700 | GO: 5634 |
| let-7a | MGAT4A | Hs.177576 | 3 | N-Glycan biosynthesis | | | |
| let-7a | MTPN | Hs.43297 | 3 | | | | |
| let-7a | MYCN | Hs.25960 | 3 | | GO: 6357 | GO: 5515<br>GO: 3700 | GO: 785<br>GO: 5634 |
| let-7a | NAB1 | Hs.107474 | 3 | | GO: 16481<br>GO: 6355<br>GO: 6350 | GO: 3676<br>GO: 16564 | GO: 5634 |
| let-7a | NCOA3 | Hs.382168 | 3 | | GO: 30521<br>GO: 45893<br>GO: 7165 | GO: 8415<br>GO: 50681<br>GO: 4402<br>GO: 5515<br>GO: 4871<br>GO: 46966<br>GO: 3713<br>GO: 30528<br>GO: 16740 | GO: 5634 |
| let-7a | NLK | Hs.208759 | 3 | Adherens junction 04520; MAPK signaling pathway 04010; Wnt signaling pathway 04310 | GO: 30178<br>GO: 6468<br>GO: 7243<br>GO: 6355 | GO: 5524<br>GO: 4707<br>GO: 287 GO: 166<br>GO: 5515<br>GO: 4674<br>GO: 4713<br>GO: 16740 | GO: 5634 |
| let-7a | NME4 | Hs.9235 | 3 | | | | |
| let-7a | NPHP3 | Hs.511991 | 3 | | | | |
| let-7a | NUMBL | Hs.326953 | 3 | Notch signaling pathway 04330 | GO: 7399 | | |
| let-7a | NUP98 | Hs.524750 | 3 | | GO: 6260<br>GO: 6999<br>GO: 6913 GO: 59<br>GO: 15031 | GO: 5515<br>GO: 17056<br>GO: 5215 | GO: 5643<br>GO: 5654 |
| let-7a | OPRM1 | Hs.2353 | 3 | Neuroactive ligand-receptor interaction 04080 | GO: 7186<br>GO: 7187<br>GO: 7610<br>GO: 8285<br>GO: 7600<br>GO: 7165 | GO: 4988<br>GO: 4872<br>GO: 1584 | GO: 5794<br>GO: 5783<br>GO: 16021<br>GO: 5887<br>GO: 5886 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| let-7a | P4HA2 | Hs.519568 | 3 | Arginine and proline metabolism 00330 | GO: 19538 | GO: 31418<br>GO: 5489<br>GO: 5506<br>GO: 46872<br>GO: 16491<br>GO: 16706<br>GO: 16702<br>GO: 4656<br>GO: 5515 | GO: 5783 |
| let-7a | PAK1 | Hs.435714 | 3 | Axon guidance 04360; Focal adhesion 04510; MAPK signaling pathway 04010; Natural killer cell mediated cytotoxicity 04650; Regulation of actin cytoskeleton 04810; T cell receptor signaling pathway 04660 | GO: 7254<br>GO: 6915<br>GO: 6468 | GO: 5524<br>GO: 166<br>GO: 5515<br>GO: 4674<br>GO: 4713<br>GO: 16740 | |
| let-7a | PANX2 | Hs.440092 | 3 | | | | GO: 5921<br>GO: 16021 |
| let-7a | PAPPA | Hs.494928 | 3 | | GO: 30154<br>GO: 7565<br>GO: 6508 | GO: 46872<br>GO: 8237<br>GO: 8270 | GO: 5615<br>GO: 16020 |
| let-7a | PAX3 | Hs.42146 | 3 | | GO: 6915<br>GO: 7275<br>GO: 7399<br>GO: 9887<br>GO: 6355<br>GO: 7605<br>GO: 6366 | GO: 3700 | GO: 5634 |
| let-7a | PBX2 | Hs.509545 | 3 | | GO: 7387<br>GO: 7388<br>GO: 6355 | GO: 5515<br>GO: 3700 | GO: 5634 |
| let-7a | PDGFB | Hs.1976 | 3 | Cytokine-cytokine receptor interaction 04060; Focal adhesion 04510; Gap junction 04540; MAPK signaling pathway 04010; Regulation of actin cytoskeleton 04810; Hemostasis 109582 | GO: 8283 GO: 74<br>GO: 9611 | GO: 8083<br>GO: 5161 | GO: 5576<br>GO: 16020 |
| let-7a | PHF8 | Hs.133352 | 3 | | GO: 6355 | GO: 46872<br>GO: 5515<br>GO: 8270 | |
| let-7a | PLAGL2 | Hs.154104 | 3 | | GO: 6355<br>GO: 6350 | GO: 46872<br>GO: 3700<br>GO: 8270 | GO: 5634 |
| let-7a | PLCB4 | Hs.472101 | 3 | Calcium signaling pathway 04020; Gap junction 04540; Inositol phosphate metabolism 00562; Phosphatidylinositol signaling system 04070; Wnt signaling pathway 04310 | GO: 7242<br>GO: 16042<br>GO: 6629 | GO: 5509<br>GO: 16787<br>GO: 4435<br>GO: 4871 | |
| let-7a | PLD3 | Hs.257008 | 3 | | GO: 8152 | GO: 3824 | |
| let-7a | PLEKHG6 | Hs.163953 | 3 | | | GO: 5085 | |
| let-7a | PLEKHO1 | Hs.438824 | 3 | | | | |
| let-7a | PLGLB2 | Hs.528525 | 3 | | | | |
| let-7a | POGZ | Hs.489873 | 3 | | GO: 7275 | GO: 3677<br>GO: 46872<br>GO: 3676<br>GO: 8270 | GO: 5634 |
| let-7a | POLH | Hs.439153 | 3 | | | | |
| let-7a | PPARGC1A | Hs.527078 | 3 | Adipocytokine signaling pathway 04920; Insulin signaling pathway 04910 | GO: 8380<br>GO: 30521<br>GO: 50873<br>GO: 1678<br>GO: 45333<br>GO: 7586 | GO: 3677<br>GO: 3723<br>GO: 16455<br>GO: 50681<br>GO: 30374<br>GO: 166 | GO: 5665<br>GO: 5634 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| | | | | | GO: 19395 | GO: 8134 | |
| | | | | | GO: 6094 | | |
| | | | | | GO: 6397 | | |
| | | | | | GO: 7005 | | |
| | | | | | GO: 46321 | | |
| | | | | | GO: 45722 | | |
| | | | | | GO: 35066 | | |
| | | | | | GO: 45893 | | |
| | | | | | GO: 6461 | | |
| | | | | | GO: 50821 | | |
| | | | | | GO: 42594 | | |
| | | | | | GO: 1659 | | |
| | | | | | GO: 6350 | | |
| | | | | | GO: 6367 | | |
| let-7a | PPP3CA | Hs.435512 | 3 | Amyotrophic lateral sclerosis 05030; Apoptosis 04210; Axon guidance 04360; B cell receptor signaling pathway 04662; Calcium signaling pathway 04020; MAPK signaling pathway 04010; Natural killer cell mediated cytotoxicity 04650; T cell receptor signaling pathway 04660; Wnt signaling pathway 04310 | GO: 6470 | GO: 5509 GO: 5516 GO: 16787 GO: 5506 GO: 4722 GO: 8270 | GO: 5955 GO: 5634 |
| let-7a | PRDM2 | Hs.371823 | 3 | | GO: 6355 | GO: 46872 GO: 3676 GO: 3700 GO: 8270 | GO: 5634 |
| let-7a | PRRX1 | Hs.283416 | 3 | | | | |
| let-7a | PTPRU | Hs.19718 | 3 | | GO: 7155 GO: 6470 GO: 7185 | GO: 16787 GO: 4725 GO: 4872 GO: 5001 | GO: 5887 GO: 16020 |
| let-7a | PYGO2 | Hs.433795 | 3 | | | | |
| let-7a | QARS | Hs.79322 | 3 | Aminoacyl-tRNA synthetases 00970; Glutamate metabolism 00251 | GO: 6425 GO: 6424 GO: 6412 | GO: 5524 GO: 4818 GO: 4819 GO: 16874 GO: 166 GO: 5515 | GO: 5737 GO: 5625 |
| let-7a | RAI16 | Hs.491223 | 3 | | | | |
| let-7a | RAPGEF6 | Hs.483329 | 3 | | | | |
| let-7a | RASL10B | Hs.437035 | 3 | | | | |
| let-7a | RB1 | Hs.408528 | 3 | Cell cycle 04110; Cell Cycle 69278 | GO: 30521 GO: 75 GO: 45786 GO: 6469 GO: 122 GO: 45893 GO: 6355 GO: 6350 | GO: 50681 GO: 5554 GO: 5515 GO: 3713 GO: 3700 | GO: 785 GO: 5634 |
| let-7a | RBM9 | Hs.282998 | 3 | Ribosomal Proteins | | | |
| let-7a | RDH10 | Hs.244940 | 3 | | | | |
| let-7a | RDX | Hs.263671 | 3 | Regulation of actin cytoskeleton 04810 | GO: 51016 GO: 7016 | GO: 3779 GO: 5488 GO: 5198 | GO: 15629 GO: 5737 GO: 5886 |
| let-7a | RGAG1 | Hs.201071 | 3 | | | | |
| let-7a | RNF20 | Hs.168095 | 3 | | GO: 16567 | GO: 46872 GO: 4842 GO: 8270 | GO: 151 |
| let-7a | RNF38 | Hs.333503 | 3 | | GO: 16567 | GO: 46872 GO: 4842 GO: 8270 | GO: 151 |
| let-7a | RNF44 | Hs.434888 | 3 | | GO: 16567 | GO: 46872 GO: 4842 GO: 8270 | GO: 151 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| let-7a | RNF5 | Hs.534342 | 3 | | GO: 16567 | GO: 46872<br>GO: 5515<br>GO: 4842<br>GO: 8270 | GO: 151 |
| let-7a | RUFY3 | Hs.7972 | 3 | | | | |
| let-7a | SCN5A | Hs.556087 | 3 | | GO: 6812<br>GO: 6936<br>GO: 8016<br>GO: 6814 | GO: 5261<br>GO: 31402<br>GO: 5248 | GO: 16021<br>GO: 16020<br>GO: 5624<br>GO: 1518 |
| let-7a | SCUBE3 | Hs.12923 | 3 | | | | |
| let-7a | SEC24C | Hs.81964 | 3 | | GO: 6888<br>GO: 6886 | GO: 3779<br>GO: 5554<br>GO: 5515 | GO: 30127<br>GO: 5795<br>GO: 5783 |
| let-7a | SEMA3F | Hs.32981 | 3 | Axon guidance 04360 | GO: 7275 | | GO: 5615 |
| let-7a | SEMA4G | Hs.567556 | 3 | Axon guidance 04360 | GO: 30154<br>GO: 7399 | GO: 4872 | GO: 16021<br>GO: 16020 |
| let-7a | SENP2 | Hs.401388 | 3 | Wnt signaling pathway 04310 | GO: 6508<br>GO: 30111<br>GO: 6512 | GO: 16929<br>GO: 8234<br>GO: 5515 | GO: 5643<br>GO: 5634 |
| let-7a | SENP5 | Hs.533124 | 3 | | | | |
| let-7a | SFRS12 | Hs.519347 | 3 | mRNA processing | | | |
| let-7a | SLC25A18 | Hs.282982 | 3 | | GO: 6810 | GO: 5488<br>GO: 15293 | GO: 16021<br>GO: 5743<br>GO: 5739 |
| let-7a | SLC25A18 | Hs.570482 | 3 | | GO: 6810 | GO: 5488<br>GO: 15293 | GO: 16021<br>GO: 5743<br>GO: 5739 |
| let-7a | SLC25A4 | Hs.246506 | 3 | Calcium signaling pathway 04020; Nucleotide metabolism 15869 | GO: 6091 GO: 2<br>GO: 6839<br>GO: 6810 | GO: 15207<br>GO: 5488<br>GO: 5215 | GO: 16021<br>GO: 5887<br>GO: 16020<br>GO: 5743<br>GO: 5739 |
| let-7a | SLC4A4 | Hs.5462 | 3 | | GO: 6820<br>GO: 6810 | GO: 5452<br>GO: 8510 | GO: 16021<br>GO: 5887<br>GO: 16020 |
| let-7a | SLC6A1 | Hs.443874 | 3 | | | | |
| let-7a | SLC6A15 | Hs.44424 | 3 | | GO: 6836 | GO: 5328<br>GO: 15293 | GO: 5887<br>GO: 16020 |
| let-7a | SLCO5A1 | Hs.443609 | 3 | | GO: 6810 | GO: 5215 | GO: 16021<br>GO: 16020 |
| let-7a | SMARCAD1 | Hs.410406 | 3 | | | | |
| let-7a | SMARCC1 | Hs.476179 | 3 | | GO: 6333<br>GO: 6338<br>GO: 45893<br>GO: 45449<br>GO: 6357 | GO: 3677<br>GO: 3682<br>GO: 5515<br>GO: 3713 | GO: 16514<br>GO: 785<br>GO: 5654<br>GO: 5634 |
| let-7a | SPATA2 | Hs.48513 | 3 | | GO: 30154<br>GO: 7283 | GO: 5554 | GO: 5737 |
| let-7a | STARD13 | Hs.507704 | 3 | | | | |
| let-7a | STRBP | Hs.287659 | 3 | | | | |
| let-7a | SYT1 | Hs.310545 | 3 | | | | |
| let-7a | TAF5 | Hs.96103 | 3 | RNA transcription | | | |
| let-7a | TARBP2 | Hs.326 | 3 | | GO: 6469<br>GO: 45946<br>GO: 45070<br>GO: 6357<br>GO: 46782 | GO: 3725<br>GO: 46982 | GO: 5622<br>GO: 5634 |
| let-7a | TBX5 | Hs.381715 | 3 | | GO: 7507<br>GO: 9653<br>GO: 45893<br>GO: 6355<br>GO: 6350 | GO: 3702<br>GO: 5515<br>GO: 3700 | GO: 5634 |
| let-7a | TGFBR1 | Hs.494622 | 3 | Adherens junction 04520; Cytokine-cytokine receptor interaction 04060; MAPK signaling pathway 04010; TGF-beta signaling pathway 04350 | GO: 6468<br>GO: 7165<br>GO: 7181<br>GO: 7178 | GO: 5524<br>GO: 287<br>GO: 30145<br>GO: 166<br>GO: 4713<br>GO: 4872<br>GO: 16740<br>GO: 5024<br>GO: 5025 | GO: 16021<br>GO: 5887<br>GO: 16020 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| let-7a | TIMM17B | Hs.30570 | 3 | | GO: 6626 | GO: 15450 | GO: 16021<br>GO: 5744<br>GO: 5739 |
| let-7a | Transcribed locus | Hs.408973 | 3 | | | | |
| let-7a | Transcribed locus | Hs.560163 | 3 | | | | |
| let-7a | TRIB2 | Hs.467751 | 3 | | GO: 6468<br>GO: 43405 | GO: 5524<br>GO: 166<br>GO: 4674<br>GO: 4713<br>GO: 16740 | GO: 5737 |
| let-7a | TRIM41 | Hs.441488 | 3 | | | | |
| let-7a | TSC22D2 | Hs.52526 | 3 | | GO: 6355 | GO: 3700 | |
| let-7a | TTLL4 | Hs.471405 | 3 | | GO: 6464 | GO: 16874<br>GO: 4835 | |
| let-7a | ULK2 | Hs.168762 | 3 | | GO: 6468 | GO: 5524<br>GO: 166<br>GO: 4674<br>GO: 4713<br>GO: 16740 | |
| let-7a | USP25 | Hs.473370 | 3 | | GO: 6508<br>GO: 6512<br>GO: 6511 | GO: 4197<br>GO: 4221 | |
| let-7a | VAV3 | Hs.267659 | 3 | B cell receptor signaling pathway 04662; Focal adhesion 04510; Natural killer cell mediated cytotoxicity 04650; Regulation of actin cytoskeleton 04810 | GO: 7242<br>GO: 7264 | GO: 5096<br>GO: 5070<br>GO: 19992<br>GO: 5085<br>GO: 46872<br>GO: 8270 | |
| let-7a | VSNL1 | Hs.444212 | 3 | | | GO: 5509 | |
| let-7a | WDFY3 | Hs.480116 | 3 | | | | |
| let-7a | WNT1 | Hs.248164 | 3 | Hedgehog signaling pathway 04340; Wnt signaling pathway 04310 | GO: 30154<br>GO: 1708<br>GO: 16477<br>GO: 7417<br>GO: 7163<br>GO: 7223<br>GO: 9653<br>GO: 7283 | GO: 5102 | GO: 5576<br>GO: 5625 |
| let-7a | XKR8 | Hs.55024 | 3 | | | | GO: 16021 |
| let-7a | ZC3H3 | Hs.521915 | 3 | | | GO: 46872<br>GO: 3676<br>GO: 8270 | |
| let-7a | ZCCHC5 | Hs.134873 | 3 | | | GO: 46872<br>GO: 3676<br>GO: 8270 | |
| let-7a | ZFYVE26 | Hs.98041 | 3 | | | GO: 3676<br>GO: 8270 | GO: 5634 |
| let-7a | ZNF318 | Hs.509718 | 3 | | | GO: 3824<br>GO: 3676<br>GO: 3735<br>GO: 8270 | GO: 5634 |
| let-7a | ZNF644 | Hs.173001 | 3 | | GO: 6355<br>GO: 6350 | GO: 3677<br>GO: 46872<br>GO: 8270 | GO: 5634 |
| let-7a | ZZZ3 | Hs.480506 | 3 | | GO: 45449 | GO: 3677<br>GO: 8270 | GO: 5634 |
| miR-182* | DOCK9 | Hs.314413 | 4 | | | | |
| miR-182* | AARS | Hs.315137 | 3 | Alanine and aspartate metabolism 00252; Aminoacyl-tRNA synthetases 00970 | GO: 6419<br>GO: 6412<br>GO: 8033 | GO: 5524<br>GO: 4813<br>GO: 16874<br>GO: 3676<br>GO: 166 GO: 49 | GO: 5737<br>GO: 5625 |
| miR-182* | ABCG1 | Hs.124649 | 3 | ABC transporters - General 02010 | GO: 42632<br>GO: 8203<br>GO: 9720<br>GO: 6869<br>GO: 10033 | GO: 5524<br>GO: 16887<br>GO: 42626<br>GO: 15196<br>GO: 166<br>GO: 15646<br>GO: 46983<br>GO: 15216 | GO: 5795<br>GO: 5783<br>GO: 5887<br>GO: 16020<br>GO: 5624 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-182* | ALDH18A1 | Hs.500645 | 3 | Urea cycle and metabolism of amino groups 00220 | GO: 8652<br>GO: 8152<br>GO: 6561 | GO: 3942<br>GO: 4349<br>GO: 4350<br>GO: 16301<br>GO: 16491<br>GO: 16740 | GO: 5739<br>GO: 19866 |
| miR-182* | BACH2 | Hs.269764 | 3 | | GO: 6355<br>GO: 6350 | GO: 3677<br>GO: 5515 | GO: 5634 |
| miR-182* | CBX3 | Hs.381189 | 3 | Circadian Exercise | GO: 6333<br>GO: 16568<br>GO: 6355<br>GO: 6350 | GO: 3682<br>GO: 5515 | GO: 785<br>GO: 5634 |
| miR-182* | CD36 | Hs.120949 | 3 | Adipocytokine signaling pathway 04920; ECM-receptor interaction 04512; Hematopoietic cell lineage 04640; Hemostasis 109582 | GO: 7596<br>GO: 7155<br>GO: 6631<br>GO: 6629<br>GO: 6810 | GO: 5515<br>GO: 4872 | GO: 5887<br>GO: 16020<br>GO: 5624 |
| miR-182* | CRLF1 | Hs.114948 | 3 | | GO: 19735 + F280 | GO: 19955<br>GO: 4872 | GO: 5615 |
| miR-182* | CXXC5 | Hs.189119 | 3 | | | GO: 3677<br>GO: 8270 | |
| miR-182* | FAT | Hs.481371 | 3 | | GO: 7155<br>GO: 7267<br>GO: 7156<br>GO: 9653 | GO: 5509<br>GO: 5515 | GO: 5887<br>GO: 16020 |
| miR-182* | FBXW11 | Hs.484138 | 3 | Hedgehog signaling pathway 04340; Ubiquitin mediated proteolysis 04120; Wnt signaling pathway 04310 | GO: 16055<br>GO: 16567 | GO: 4842 | GO: 151 |
| miR-182* | FYCO1 | Hs.200227 | 3 | | | | |
| miR-182* | KCMF1 | Hs.345694 | 3 | | | | |
| miR-182* | GALNT1 | Hs.514806 | 3 | O-Glycan biosynthesis 00512 | GO: 6493 | GO: 5509<br>GO: 30145<br>GO: 4653<br>GO: 5529<br>GO: 16757 | GO: 5795<br>GO: 16021 |
| miR-182* | HDAC7A | Hs.200063 | 3 | Cell cycle 04110 | GO: 30183<br>GO: 16568<br>GO: 6954<br>GO: 45843<br>GO: 7399 GO: 74<br>GO: 6355<br>GO: 6350 | GO: 4407<br>GO: 16787<br>GO: 16566<br>GO: 8134 | GO: 5737<br>GO: 118<br>GO: 5634 |
| miR-182* | HDHD2 | Hs.465041 | 3 | | | | |
| miR-182* | HOXB4 | Hs.532669 | 3 | | GO: 7275<br>GO: 6355 | GO: 3700 | GO: 5634 |
| miR-182* | HRMT1L4 | Hs.504530 | 3 | Aminophosphonate metabolism 00440; Androgen and estrogen metabolism 00150; Histidine metabolism 00340; Nitrobenzene degradation 00626; Selenoamino acid metabolism 00450; Tryptophan metabolism 00380; Tyrosine metabolism 00350 | | GO: 8757<br>GO: 16740 | GO: 5634 |
| miR-182* | ITGA10 | Hs.158237 | 3 | ECM-receptor interaction 04512; Focal adhesion 04510; Regulation of actin cytoskeleton 04810 | GO: 7155<br>GO: 7160<br>GO: 7229 | GO: 5509<br>GO: 5518<br>GO: 287<br>GO: 4872 | GO: 16021<br>GO: 8305 |
| miR-182* | LGI1 | Hs.533670 | 3 | | GO: 8283<br>GO: 7399 | | |
| miR-182* | MAPK9 | Hs.484371 | 3 | Adipocytokine signaling pathway 04920; Focal adhesion 04510; Insulin signaling pathway 04910; MAPK signaling pathway 04010; Toll-like | GO: 7254<br>GO: 6468<br>GO: 6950 | GO: 5524<br>GO: 4705<br>GO: 4707<br>GO: 166<br>GO: 5515<br>GO: 4674 | |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| | | | | receptor signaling pathway 04620; Type II diabetes mellitus 04930; Wnt signaling pathway 04310 | | GO: 4713 GO: 16740 | |
| miR-182* | PLA2G6 | Hs.170479 | 3 | Glycerophospholipid metabolism 00564; MAPK signaling pathway 04010; Prostaglandin and leukotriene metabolism 00590 | GO: 16042 GO: 6644 | GO: 16787 GO: 4623 | GO: 5737 GO: 16020 |
| miR-182* | PLAGL2 | Hs.154104 | 3 | | GO: 6355 GO: 6350 | GO: 46872 GO: 3700 GO: 8270 | GO: 5634 |
| miR-182* | PLCL2 | Hs.202010 | 3 | | | | |
| miR-182* | RAB5A | Hs.475663 | 3 | | GO: 6897 GO: 6886 GO: 7264 | GO: 5525 GO: 3924 GO: 166 GO: 5515 | GO: 5769 |
| miR-182* | RAB6A | Hs.503222 | 3 | | GO: 6888 GO: 15031 GO: 7264 | GO: 5525 GO: 3924 GO: 166 GO: 5515 | GO: 5795 |
| miR-182* | RBM12 | Hs.246413 | 3 | | | | |
| miR-182* | RPS6KA1 | Hs.149957 | 3 | Ribosomal Proteins;; Calcium signaling pathway; Phosphatidylinositol signaling system | GO: 6468 GO: 7165 | GO: 5524 GO: 166 GO: 4672 GO: 4674 GO: 4713 GO: 3735 GO: 16740 | |
| miR-182* | SBF1 | Hs.449098 | 3 | | GO: 46839 GO: 6470 | GO: 4437 GO: 8138 | GO: 16021 GO: 5634 |
| miR-182* | SLC18A1 | Hs.158322 | 3 | | GO: 15893 GO: 15844 | GO: 15238 GO: 8504 GO: 15293 | GO: 16021 GO: 5624 |
| miR-182* | SMAD7 | Hs.465087 | 3 | TGF-beta signaling pathway 04350 | GO: 6355 GO: 6950 GO: 6350 GO: 7179 | GO: 5515 GO: 5076 GO: 30617 | GO: 5634 |
| miR-182* | TACR3 | Hs.942 | 3 | Calcium signaling pathway 04020; Neuroactive ligand-receptor interaction 04080 | GO: 7165 GO: 7217 | GO: 4872 GO: 1584 GO: 4995 | GO: 5887 GO: 5886 |
| miR-182* | TCERG1 | Hs.443465 | 3 | | GO: 6355 GO: 6350 GO: 6366 | GO: 3702 GO: 5515 GO: 3713 | GO: 5634 |
| miR-182* | TFIP11 | Hs.20225 | 3 | | GO: 30154 GO: 30198 GO: 1503 GO: 45045 | GO: 3676 GO: 5515 | GO: 5634 |
| miR-182* | TP53INP2 | Hs.516994 | 3 | | | | |
| miR-182* | UBE2B | Hs.385986 | 3 | Ubiquitin mediated proteolysis; | GO: 6281 GO: 6512 | GO: 16874 GO: 8642 GO: 4842 | GO: 16020 GO: 5634 |
| miR-182* | VAT1 | Hs.514199 | 3 | | GO: 16049 | GO: 3677 GO: 16491 GO: 8270 | GO: 16021 GO: 5634 GO: 8021 |
| miR-182* | ZFP36L2 | Hs.503093 | 3 | | GO: 8283 | GO: 46872 GO: 3676 GO: 3700 GO: 8270 | GO: 5634 |
| miR-182* | ZIC3 | Hs.111227 | 3 | | GO: 7368 GO: 6355 GO: 6350 | GO: 3677 GO: 46872 GO: 8270 | GO: 5634 |
| miR-372 | ATXN1 | Hs.434961 | 4 | | | GO: 3723 | GO: 5737 GO: 5634 |
| miR-372 | POLH | Hs.439153 | 4 | | | | |
| miR-372 | BCL11B | Hs.510396 | 4 | | GO: 6355 GO: 6350 | GO: 46872 GO: 3676 GO: 8270 | GO: 5634 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-372 | DPYSL5 | Hs.299315 | 4 | Axon guidance 04360 | GO: 7411<br>GO: 7399<br>GO: 7165 | GO: 16787 | |
| miR-372 | INHBB | Hs.1735 | 4 | Cytokine-cytokine receptor interaction 04060; TGF-beta signaling pathway 04350 | GO: 30154<br>GO: 6952<br>GO: 40007<br>GO: 46882<br>GO: 48178<br>GO: 1541 | GO: 5125<br>GO: 8083<br>GO: 5179<br>GO: 46789<br>GO: 42803 | GO: 5576 |
| miR-372 | MAP3K11 | Hs.502872 | 4 | ; Calcium signaling pathway | GO: 80 GO: 7257<br>GO: 8283<br>GO: 7017<br>GO: 46777<br>GO: 51259 | GO: 5524<br>GO: 4706<br>GO: 166<br>GO: 5515<br>GO: 42803<br>GO: 4674<br>GO: 4713 | GO: 5813<br>GO: 5874 |
| miR-372 | MYCN | Hs.25960 | 4 | | GO: 6357 | GO: 5515<br>GO: 3700 | GO: 785<br>GO: 5634 |
| miR-372 | NEUROD6 | Hs.45152 | 4 | | GO: 6355 | GO: 3677<br>GO: 30528 | GO: 5634 |
| miR-372 | NFIB | Hs.370359 | 4 | | GO: 6260<br>GO: 6355<br>GO: 6350 | GO: 3700 | GO: 5634 |
| miR-372 | PARP8 | Hs.369581 | 4 | | | | |
| miR-372 | CDNA FLJ38785 fis | Hs.406990 | 4 | | | | |
| miR-372 | RBBP7 | Hs.495755 | 4 | | GO: 8283<br>GO: 7275 | GO: 5515 | GO: 5634 |
| miR-372 | SS18L1 | Hs.154429 | 4 | | | GO: 5515 | |
| miR-372 | TLE4 | Hs.444213 | 4 | | GO: 4 GO: 7222<br>GO: 6355 | GO: 5554 | GO: 5634 |
| miR-372 | ADAM9 | Hs.2442 | 3 | | GO: 7243<br>GO: 6508 | GO: 17124<br>GO: 5178<br>GO: 46872<br>GO: 4222<br>GO: 5515<br>GO: 19901<br>GO: 8270 | GO: 5887 |
| miR-372 | AEBP2 | Hs.126497 | 3 | | | | |
| miR-372 | AMPD2 | Hs.82927 | 3 | Purine metabolism | | | |
| miR-372 | ANK2 | Hs.567235 | 3 | Ribosomal Proteins | | | |
| miR-372 | APBB2 | Hs.479602 | 3 | | GO: 30048<br>GO: 7409<br>GO: 7050<br>GO: 7242<br>GO: 45749<br>GO: 30308<br>GO: 50821 | GO: 1540<br>GO: 35035<br>GO: 8134 | GO: 30426<br>GO: 30027<br>GO: 16020<br>GO: 5634<br>GO: 45202 |
| miR-372 | APP | Hs.434980 | 3 | Alzheimer's disease 05010; Neurodegenerative Disorders 01510; Hemostasis 109582 | GO: 7219<br>GO: 6915<br>GO: 7155<br>GO: 6878<br>GO: 6897<br>GO: 50905 | GO: 5507<br>GO: 8201<br>GO: 5506<br>GO: 46872<br>GO: 5515<br>GO: 4867<br>GO: 8270 | GO: 9986<br>GO: 5905<br>GO: 5576<br>GO: 5887 |
| miR-372 | ARHGAP9 | Hs.437126 | 3 | | | GO: 5096 | |
| miR-372 | ARHGEF10 | Hs.98594 | 3 | | | | |
| miR-372 | ARID4A | Hs.161000 | 3 | | GO: 6333<br>GO: 45892<br>GO: 6350<br>GO: 6366 | GO: 3682<br>GO: 5515<br>GO: 3700<br>GO: 16564 | GO: 785<br>GO: 5634<br>GO: 17053 |
| miR-372 | ARID4B | Hs.533633 | 3 | | | GO: 3677<br>GO: 3676 | GO: 5622<br>GO: 5634 |
| miR-372 | ATP2B2 | Hs.268942 | 3 | Calcium signaling pathway 04020 | GO: 6816<br>GO: 6812<br>GO: 8152 | GO: 5524<br>GO: 5509<br>GO: 5388<br>GO: 5516<br>GO: 16787<br>GO: 16820 | GO: 16021<br>GO: 5886 |
| miR-372 | ATP2B4 | Hs.343522 | 3 | Calcium signaling pathway 04020 | GO: 6816<br>GO: 6812<br>GO: 8152 | GO: 5524<br>GO: 5509<br>GO: 5388 | GO: 5887<br>GO: 5886 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| | | | | | | GO: 5516 | |
| | | | | | | GO: 16787 | |
| | | | | | | GO: 16820 | |
| miR-372 | BAHD1 | Hs.22109 | 3 | | | | |
| miR-372 | BCL11A | Hs.370549 | 3 | | GO: 30097 | GO: 46872 | GO: 5737 |
| | | | | | GO: 6355 | GO: 3676 | GO: 5634 |
| | | | | | GO: 6350 | GO: 8270 | |
| miR-372 | BRP44L | Hs.172755 | 3 | | | GO: 5554 | |
| miR-372 | BTG1 | Hs.255935 | 3 | Circadian Exercise | GO: 16477 | GO: 19900 | GO: 5737 |
| | | | | | GO: 30308 | GO: 3712 | GO: 5634 |
| | | | | | GO: 8285 | | |
| | | | | | GO: 45766 | | |
| | | | | | GO: 45603 | | |
| | | | | | GO: 43085 | | |
| miR-372 | C15orf17 | Hs.367690 | 3 | | | | |
| miR-372 | C16orf28 | Hs643536 | 3 | | GO: 16567 | GO: 4842 | GO: 151 |
| | | | | | | GO: 8270 | |
| miR-372 | CCND2 | Hs.376071 | 3 | Cell cycle 04110; Focal adhesion 04510; Jak-STAT signaling pathway 04630; Wnt signaling pathway 04310; Cell Cycle 69278 | GO: 51301 GO: 74 | | GO: 5634 |
| miR-372 | CDC2L6 | Hs.159118 | 3 | | | | |
| miR-372 | CFL2 | Hs.180141 | 3 | G13 Signaling Pathway | | | |
| miR-372 | COL23A1 | Hs.413494 | 3 | | | | |
| miR-372 | TNXB | Hs.42853 | 3 | G1 to S cell cycle; Smooth muscle contraction | | | |
| miR-372 | CRIM1 | Hs.332847 | 3 | | | | |
| miR-372 | CUL4A | Hs.339735 | 3 | | | | |
| miR-372 | DAZAP2 | Hs.369761 | 3 | Circadian Exercise | | | |
| miR-372 | DMTF1 | Hs.558441 | 3 | | | | |
| miR-372 | E2F5 | Hs.445758 | 3 | Cell cycle 04110; TGF-beta signaling pathway 04350; Cell Cycle 69278 | GO: 74 GO: 6355 GO: 6350 | GO: 5515 GO: 3700 | GO: 5634 GO: 5667 |
| miR-372 | EIF2C1 | Hs.22867 | 3 | | GO: 6412 | GO: 5515 | GO: 5850 |
| | | | | | GO: 6446 | GO: 3743 | |
| miR-372 | EPAS1 | Hs.468410 | 3 | | GO: 1525 | GO: 3705 | GO: 5634 |
| | | | | | GO: 30154 | GO: 35035 | |
| | | | | | GO: 6355 | GO: 5515 | |
| | | | | | GO: 1666 | GO: 4871 | |
| | | | | | GO: 7165 | GO: 3713 | |
| | | | | | GO: 6366 | | |
| miR-372 | EPHA2 | Hs.171596 | 3 | Axon guidance 04360 | GO: 7275 | GO: 5524 | GO: 5887 |
| | | | | | GO: 6468 | GO: 5003 | GO: 16020 |
| | | | | | GO: 7165 | GO: 166 | |
| | | | | | GO: 7169 | GO: 4674 | |
| | | | | | | GO: 4872 | |
| | | | | | | GO: 16740 | |
| miR-372 | ERBB4 | Hs.390729 | 3 | Calcium signaling pathway 04020; Dorso-ventral axis formation 04320 | GO: 8283 | GO: 5524 | GO: 5887 |
| | | | | | GO: 7275 | GO: 5006 | GO: 16020 |
| | | | | | GO: 6468 | GO: 166 | |
| | | | | | GO: 7169 | GO: 5515 | |
| | | | | | | GO: 4872 | |
| | | | | | | GO: 16740 | |
| miR-372 | FBXL11 | Hs.124147 | 3 | | GO: 6355 | GO: 3677 | |
| | | | | | GO: 6512 | GO: 46872 | |
| | | | | | | GO: 5515 | |
| | | | | | | GO: 8270 | |
| miR-372 | Transcribed locus | Hs.246781 | 3 | | | | |
| miR-372 | FNDC3A | Hs.508010 | 3 | ECM-receptor interaction 04512 | | | |
| miR-372 | GCAT | Hs.54609 | 3 | Glycine, serine and threonine metabolism 00260 | GO: 6520 | GO: 8415 | GO: 5739 |
| | | | | | GO: 9058 | GO: 8890 | |
| | | | | | | GO: 16874 | |
| | | | | | | GO: 16769 | |
| miR-372 | GPR161 | Hs.271809 | 3 | GPCRDB Class A Rhodopsin-like2 | | | |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-372 | GPR6 | Hs.46332 | 3 | GPCRDB Class A Rhodopsin-like | GO: 7186<br>GO: 7165 | GO: 16526<br>GO: 4872<br>GO: 1584 | GO: 5887 |
| miR-372 | HBP1 | Hs.162032 | 3 | | GO: 16055<br>GO: 6355<br>GO: 6350 | GO: 3677 | GO: 5634 |
| miR-372 | HIC2 | Hs.517434 | 3 | | GO: 45892<br>GO: 6350 | GO: 3677<br>GO: 46872<br>GO: 8022<br>GO: 8270 | GO: 5634 |
| miR-372 | HNRPH3 | Hs.198158 | 3 | | | | |
| miR-372 | IRF2 | Hs.374097 | 3 | Apoptosis | GO: 8283<br>GO: 6955<br>GO: 122<br>GO: 6355<br>GO: 6350 | GO: 3702<br>GO: 3700 | GO: 5634 |
| miR-372 | KCNMA1 | Hs.568865 | 3 | | | | |
| miR-372 | KIF3B | Hs.369670 | 3 | | | | |
| miR-372 | KLF12 | Hs.373857 | 3 | | GO: 6357<br>GO: 6350 | GO: 46872<br>GO: 3714<br>GO: 3700<br>GO: 8270 | GO: 5634 |
| miR-372 | LATS2 | Hs.78960 | 3 | | GO: 82 GO: 7049<br>GO: 51301<br>GO: 9755<br>GO: 7067<br>GO: 45736<br>GO: 6468 | GO: 5524<br>GO: 287 GO: 166<br>GO: 4674<br>GO: 4713<br>GO: 16740 | GO: 5634<br>GO: 922 |
| miR-372 | LOC641518 | Hs.535760 | 3 | TGF Beta Signaling Pathway | | | |
| miR-372 | LEF1 | Hs.555947 | 3 | Adherens junction 04520; Wnt signaling pathway 04310 | GO: 16055<br>GO: 6355<br>GO: 6350 | GO: 3677 | GO: 5634 |
| miR-372 | LHX6 | Hs.103137 | 3 | | GO: 7420<br>GO: 6355 | GO: 46872<br>GO: 3700<br>GO: 8270 | GO: 5634 |
| miR-372 | LUC7L2 | Hs.530118 | 3 | | | GO: 46872<br>GO: 8270 | |
| miR-372 | MBNL2 | Hs.125715 | 3 | | | | |
| miR-372 | MEF2C | Hs.444409 | 3 | MAPK signaling pathway 04010 | GO: 7517<br>GO: 7399<br>GO: 6355<br>GO: 6350<br>GO: 6366 | GO: 3702<br>GO: 3713<br>GO: 3700 | GO: 5634 |
| miR-372 | MKRN1 | Hs.490347 | 3 | | GO: 4 GO: 16567 | GO: 46872<br>GO: 5554<br>GO: 3676<br>GO: 5515<br>GO: 4842<br>GO: 8270 | GO: 8372<br>GO: 151 |
| miR-372 | MTMR3 | Hs.474536 | 3 | | GO: 46839<br>GO: 6470 | GO: 16787<br>GO: 4437<br>GO: 46872<br>GO: 4722<br>GO: 4725<br>GO: 8270 | GO: 5737<br>GO: 5624 |
| miR-372 | NEK9 | Hs.7200 | 3 | | GO: 7049<br>GO: 51301<br>GO: 7067<br>GO: 6468 | GO: 5524<br>GO: 287 GO: 166<br>GO: 4674<br>GO: 16740 | |
| miR-372 | NEUROD1 | Hs.72981 | 3 | | GO: 30154<br>GO: 7399<br>GO: 6355 | GO: 3677<br>GO: 3702 | GO: 5634 |
| miR-372 | NPAS3 | Hs.509113 | 3 | | GO: 6355<br>GO: 7165 | GO: 3677<br>GO: 4871<br>GO: 30528 | GO: 5634 |
| miR-372 | NR4A2 | Hs.165258 | 3 | Nuclear Receptors | GO: 19735)<br>GO: 6355<br>GO: 7165<br>GO: 6350 | GO: 4879<br>GO: 46872<br>GO: 3707<br>GO: 3700<br>GO: 8270 | GO: 5634 |
| miR-372 | NR4A3 | Hs.279522 | 3 | Hypertrophy model | GO: 4 GO: 6355<br>GO: 6350 | GO: 5488<br>GO: 4879 | GO: 5634 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| | | | | | | GO: 46872 | |
| | | | | | | GO: 3707 | |
| | | | | | | GO: 4887 | |
| | | | | | | GO: 3700 | |
| | | | | | | GO: 8270 | |
| miR-372 | OSBPL8 | Hs.430849 | 3 | | GO: 6869 | | |
| | | | | | GO: 8202 | | |
| miR-372 | PAPOLA | Hs.253726 | 3 | mRNA processing | | | |
| miR-372 | PCAF | Hs.533055 | 3 | | | | |
| miR-372 | PCDHA4 | Hs.199343 | 3 | | | | |
| miR-372 | PERQ1 | Hs.414396 | 3 | | | | |
| miR-372 | PHF1 | Hs.166204 | 3 | | GO: 6355 | GO: 46872 | GO: 5634 |
| | | | | | | GO: 3676 | |
| | | | | | | GO: 5515 | |
| | | | | | | GO: 3700 | |
| | | | | | | GO: 8270 | |
| miR-372 | PHF2 | Hs.211441 | 3 | | GO: 6355 | GO: 46872 | GO: 5634 |
| | | | | | | GO: 5515 | |
| | | | | | | GO: 3700 | |
| | | | | | | GO: 8270 | |
| miR-372 | PLAG1 | Hs.14968 | 3 | | | GO: 46872 | GO: 5634 |
| | | | | | | GO: 3676 | |
| | | | | | | GO: 3700 | |
| | | | | | | GO: 8270 | |
| miR-372 | PLAGL2 | Hs.154104 | 3 | | GO: 6355 | GO: 46872 | GO: 5634 |
| | | | | | GO: 6350 | GO: 3700 | |
| | | | | | | GO: 8270 | |
| miR-372 | POLK | Hs.135756 | 3 | DNA polymerase 03030 | GO: 6281 | GO: 3677 | GO: 5634 |
| | | | | | GO: 6260 | GO: 3887 | |
| | | | | | GO: 6280 | GO: 287 | |
| | | | | | | GO: 16740 | |
| | | | | | | GO: 8270 | |
| miR-372 | POLQ | Hs.241517 | 3 | Purine metabolism; Pyrimidine metabolism; DNA polymerase | | | |
| miR-372 | PPP3CA | Hs.435512 | 3 | Amyotrophic lateral sclerosis 05030; Apoptosis 04210; Axon guidance 04360; B cell receptor signaling pathway 04662; Calcium signaling pathway 04020; MAPK signaling pathway | GO: 6470 | GO: 5509 | GO: 5955 |
| | | | | | | GO: 5516 | GO: 5634 |
| | | | | | | GO: 16787 | |
| | | | | | | GO: 5506 | |
| | | | | | | GO: 4722 | |
| | | | | | | GO: 8270 | |
| miR-372 | PPP3CA | Hs.535457 | 3 | G Protein Signaling; Calcium signaling pathway | | | |
| miR-372 | PPP6C | Hs.495128 | 3 | | GO: 82 GO: 6470 | GO: 16787 | |
| | | | | | | GO: 5506 | |
| | | | | | | GO: 30145 | |
| | | | | | | GO: 46872 | |
| | | | | | | GO: 4722 | |
| miR-372 | PRDM4 | Hs.506655 | 3 | | GO: 8283 | GO: 3677 | GO: 5634 |
| | | | | | GO: 6355 | GO: 3702 | |
| | | | | | GO: 7165 | GO: 46872 | |
| | | | | | GO: 6350 | GO: 8270 | |
| | | | | | GO: 6366 | | |
| miR-372 | PRRX1 | Hs.283416 | 3 | | | | |
| miR-372 | PUM1 | Hs.144795 | 3 | | GO: 6812 | GO: 5509 | GO: 16021 |
| | | | | | GO: 6936 | GO: 15269 | GO: 16020 |
| | | | | | GO: 7269 | GO: 287 | GO: 8076 |
| | | | | | GO: 6813 | GO: 30955 | |
| | | | | | GO: 7268 | GO: 5515 | |
| | | | | | | GO: 5249 | |
| miR-372 | RAB11A | Hs.321541 | 3 | | | | |
| miR-372 | RAB6A | Hs.503222 | 3 | | GO: 6888 | GO: 5525 | GO: 5795 |
| | | | | | GO: 15031 | GO: 3924 | |
| | | | | | GO: 7264 | GO: 166 | |
| | | | | | | GO: 5515 | |
| miR-372 | RAB6C | Hs.535586 | 3 | | GO: 6886 | GO: 5525 | GO: 5622 |
| | | | | | GO: 42493 | GO: 3924 | |
| | | | | | GO: 7264 | GO: 166 | |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-372 | RAB7 | Hs.15738 | 3 | | GO: 6897<br>GO: 6886<br>GO: 7264 | | |
| miR-372 | RAB7B | Hs.534612 | 3 | | GO: 6886<br>GO: 7264 | GO: 5525<br>GO: 166 | GO: 5764 |
| miR-372 | RABGAP1 | Hs.271341 | 3 | | | | |
| miR-372 | RALGDS | Hs.106185 | 3 | | GO: 7264 | GO: 5085 | GO: 8372 |
| miR-372 | RBL2 | Hs.513609 | 3 | Cell cycle 04110; TGF-beta signaling pathway 04350 | GO: 7049<br>GO: 45786<br>GO: 6355<br>GO: 6350 | GO: 3677<br>GO: 5515 | GO: 5634 |
| miR-372 | RBM17 | Hs.498548 | 3 | mRNA processing | | | |
| miR-372 | RDBP | Hs.423935 | 3 | Gene Expression 74160; Transcription 74159 | GO: 4 GO: 6355<br>GO: 6350 | GO: 3723<br>GO: 166<br>GO: 5515 | GO: 5634 |
| miR-372 | RGL1 | Hs.497148 | 3 | | GO: 7264 | GO: 8321<br>GO: 5515 | GO: 8372 |
| miR-372 | RHOC | Hs.514941 | 3 | | | | |
| miR-372 | RPS6KA1 | Hs.149957 | 3 | Ribosomal Proteins; Calcium signaling pathway; Phosphatidylinositol signaling system | GO: 6468<br>GO: 7165 | GO: 5524<br>GO: 166<br>GO: 4672<br>GO: 4674<br>GO: 4713<br>GO: 3735<br>GO: 16740 | |
| miR-372 | RPS6KA5 | Hs.510225 | 3 | MAPK signaling pathway 04010 | GO: 7173<br>GO: 16572<br>GO: 6468<br>GO: 7243<br>GO: 6508<br>GO: 6355<br>GO: 422 | GO: 5524<br>GO: 3824<br>GO: 8237<br>GO: 166<br>GO: 5515<br>GO: 4674<br>GO: 4713<br>GO: 16740 | GO: 5634 |
| miR-372 | RSBN1 | Hs.486285 | 3 | | | | |
| miR-372 | RTN1 | Hs.368626 | 3 | | GO: 30182<br>GO: 7165 | GO: 5554<br>GO: 4871 | GO: 5783<br>GO: 30176<br>GO: 16021 |
| miR-372 | RUNX1 | Hs.149261 | 3 | | GO: 7275<br>GO: 45944<br>GO: 6355<br>GO: 6350 | GO: 5524<br>GO: 5515<br>GO: 3700<br>GO: 16563 | GO: 5634 |
| miR-372 | SAR1B | Hs.432984 | 3 | | GO: 6888<br>GO: 6886<br>GO: 7264 | GO: 5525<br>GO: 287 GO: 166 | GO: 5795<br>GO: 5783<br>GO: 16020 |
| miR-372 | SART1 | Hs.502883 | 3 | | | | GO: 5829 |
| miR-372 | SENP1 | Hs.371957 | 3 | | GO: 6508<br>GO: 6512 | GO: 8234<br>GO: 4175 | GO: 5634 |
| miR-372 | SLC2A4 | Hs.380691 | 3 | Adipocytokine signaling pathway 04920; Insulin signaling pathway 04910; Type II diabetes mellitus 04930; Metabolism of sugars 71387 | GO: 5975<br>GO: 8643<br>GO: 42593<br>GO: 15758 | GO: 5355<br>GO: 5515<br>GO: 5351<br>GO: 5215 | GO: 9897<br>GO: 5887<br>GO: 16020<br>GO: 5624<br>GO: 48471<br>GO: 12506 |
| miR-372 | SLITRK3 | Hs.101745 | 3 | | | | GO: 16021 |
| miR-372 | STAT3 | Hs.463059 | 3 | Adipocytokine signaling pathway 04920; Jak-STAT signaling pathway 04630 | GO: 7259<br>GO: 6953<br>GO: 6928<br>GO: 19221<br>GO: 7242<br>GO: 122 | GO: 5509<br>GO: 5062<br>GO: 4871<br>GO: 3700<br>GO: 8134 | GO: 5737<br>GO: 5634 |
| miR-372 | SUV39H1 | Hs.522639 | 3 | Lysine degradation 00310 | GO: 67 GO: 6333<br>GO: 16568 | GO: 8757<br>GO: 3682<br>GO: 46974<br>GO: 18024<br>GO: 5515<br>GO: 167 | GO: 785<br>GO: 794<br>GO: 5634 |
| miR-372 | SUV420H1 | Hs.503001 | 3 | | | | |
| miR-372 | TIPARP | Hs.12813 | 3 | | | | |
| miR-372 | TP53INP2 | Hs.516994 | 3 | | | | |
| miR-372 | TRPS1 | Hs.253594 | 3 | | GO: 6607<br>GO: 6355<br>GO: 1501 | GO: 46872<br>GO: 3700<br>GO: 8270 | GO: 5634 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| | | | | | GO: 6350 GO: 6366 | | |
| miR-372 | TRPV6 | Hs.302740 | 3 | | | | |
| miR-372 | TUSC2 | Hs.517981 | 3 | | | | |
| miR-372 | UBE2B | Hs.385986 | 3 | Ubiquitin mediated proteolysis | GO: 6281 GO: 6512 | GO: 16874 GO: 8642 GO: 4842 | GO: 16020 GO: 5634 |
| miR-372 | VLDLR | Hs.370422 | 3 | | GO: 8203 GO: 6897 GO: 6629 GO: 6869 GO: 7613 GO: 7399 GO: 7165 GO: 8202 | GO: 5509 GO: 5319 GO: 5041 GO: 4872 | GO: 5905 GO: 16021 GO: 16020 GO: 5624 |
| miR-372 | YWHAZ | Hs.492407 | 3 | Cell cycle 04110 | | GO: 19904 | |
| miR-372 | ZBTB4 | Hs.35096 | 3 | | | | |
| miR-372 | ZDHHC17 | Hs.4014 | 3 | | GO: 42953 GO: 43123 | GO: 8415 GO: 46872 GO: 5515 GO: 19706 GO: 4871 GO: 16740 GO: 8270 | GO: 5795 GO: 16021 GO: 16020 |
| miR-372 | ZNF238 | Hs.69997 | 3 | | GO: 7001) GO: 122 GO: 6355 GO: 6350 GO: 6810 | GO: 46872 GO: 3676 GO: 5515 GO: 3704 GO: 3700 GO: 8270 | GO: 228 GO: 5634 |
| miR-372 | ZNF385 | Hs.505653 | 3 | | | | |
| miR-372 | ZNF532 | Hs.529023 | 3 | | | GO: 3677 GO: 46872 GO: 8270 | GO: 5634 |
| miR-372 | PRDM8 | Hs.373642 | 3 | | GO: 6355 GO: 6350 | GO: 3677 GO: 46872 GO: 3676 GO: 8270 | GO: 5634 |
| miR-372 | DDOST | Hs.523145 | 3 | N-Glycan biosynthesis 00510 | GO: 18279 | GO: 4579 GO: 16740 | GO: 5789 GO: 16021 |
| miR-372 | ZFP91 | Hs.524920 | 3 | | | | |
| miR-372 | FBXL4 | Hs.536850 | 3 | | GO: 6512 GO: 6511 | | GO: 5634 GO: 151 |
| miR-221 | PHF1 | Hs.166204 | 5 | | GO: 6355 | GO: 46872 GO: 3676 GO: 5515 GO: 3700 GO: 8270 | GO: 5634 |
| miR-221 | PHF2 | Hs.211441 | 5 | | GO: 6355 | GO: 46872 GO: 5515 GO: 3700 GO: 8270 | GO: 5634 |
| miR-221 | ATP1A4 | Hs.367953 | 5 | Calcium regulation in cardiac cells | GO: 15991 GO: 6812 GO: 30641 GO: 8152 GO: 6813 GO: 6814 GO: 30317 | GO: 5524 GO: 15662 GO: 3824 GO: 16787 GO: 16820 GO: 287 GO: 15077 GO: 166 GO: 30955 GO: 31402 GO: 5391 | GO: 16020 GO: 5890 |
| miR-221 | ZNF385 | Hs.505653 | 5 | | | | |
| miR-221 | TCF12 | Hs.511504 | 5 | | GO: 7275 GO: 6955 GO: 7517 GO: 45449 GO: 6357 | GO: 3677 GO: 3702 GO: 30528 | GO: 5634 |
| miR-221 | MESDC1 | Hs.513071 | 5 | | | | |
| miR-221 | KHDRBS2 | Hs.519794 | 5 | | | | |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-221 | C20orf23 | Hs.101774 | 4 | | GO: 7242<br>GO: 7018 | GO: 5524<br>GO: 3777<br>GO: 166 | GO: 5874<br>GO: 5875 |
| miR-221 | SLC25A37 | Hs.122514 | 4 | | | | |
| miR-221 | MAPK10 | Hs.125503 | 4 | Apoptosis; Apoptosis; G13 Signaling Pathway; Integrin-mediated cell adhesion; MAPK Cascade; Wnt signaling | | | |
| miR-221 | ARF4 | Hs.148330 | 4 | Cholera - Infection 05110 | GO: 6888<br>GO: 6886<br>GO: 7264 | GO: 5525<br>GO: 3924<br>GO: 8047<br>GO: 166 | GO: 5795 |
| miR-221 | VAPB | Hs.182625 | 4 | | GO: 6461 | GO: 5554<br>GO: 5198 | GO: 5887 |
| miR-221 | DMRT3 | Hs.189174 | 4 | | | | |
| miR-221 | PCDHA6 | Hs.199343 | 4 | | GO: 7155<br>GO: 7156<br>GO: 7399 | GO: 5509<br>GO: 5515 | GO: 5887<br>GO: 16020 |
| miR-221 | NLK | Hs.208759 | 4 | | | | |
| miR-221 | FOS | Hs.25647 | 4 | B cell receptor signaling pathway 04662; MAPK signaling pathway 04010; T cell receptor signaling pathway 04660; Toll-like receptor signaling pathway 04620 | GO: 6306<br>GO: 6954<br>GO: 6357 | GO: 3677<br>GO: 3704 | GO: 5634 |
| miR-221 | DHDDS | Hs.369385 | 4 | N-Glycan biosynthesis 00510 | GO: 8152 | GO: 16740 | |
| miR-221 | ATP1A1 | Hs.371889 | 4 | | GO: 15991<br>GO: 6812<br>GO: 30641<br>GO: 8152<br>GO: 6813<br>GO: 6814<br>GO: 30317 | GO: 5524<br>GO: 15662<br>GO: 16787<br>GO: 16820<br>GO: 287<br>GO: 15077<br>GO: 166<br>GO: 30955<br>GO: 5515<br>GO: 31402<br>GO: 5391 | GO: 16020<br>GO: 5624<br>GO: 5890 |
| miR-221 | MGC16179 | Hs.371889 | 4 | | | | |
| miR-221 | ANKHD1 | Hs.434219 | 4 | | | | |
| miR-221 | PAK1 | Hs.435714 | 4 | Integrin-mediated cell adhesion | | | |
| miR-221 | IRX5 | Hs.435730 | 4 | | GO: 6355 | GO: 3700 | GO: 5634 |
| miR-221 | PKN1 | Hs.466044 | 4 | G13 Signaling Pathway | GO: 7257<br>GO: 6468<br>GO: 7165 | GO: 5524<br>GO: 166<br>GO: 5515<br>GO: 4674<br>GO: 4713<br>GO: 16740 | GO: 5622 |
| miR-221 | GPI | Hs.466471 | 4 | Glycolysis/Gluconeogenesis 00010; Pentose phosphate pathway 00030; Starch and sucrose metabolism 00500; Metabolism of sugars 71387 | GO: 5975<br>GO: 6094<br>GO: 6096<br>GO: 7599<br>GO: 6959<br>GO: 7399 | GO: 5125<br>GO: 4347<br>GO: 8083<br>GO: 16853 | GO: 5615 |
| miR-221 | MAP3K10 | Hs.466743 | 4 | MAPK signaling pathway 04010 | GO: 7257<br>GO: 6917<br>GO: 46777<br>GO: 7165 | GO: 5524<br>GO: 4706<br>GO: 166<br>GO: 42803<br>GO: 4674<br>GO: 4713<br>GO: 16740 | |
| miR-221 | ARID1A | Hs.468972 | 4 | | GO: 30521<br>GO: 16568<br>GO: 48096<br>GO: 30520<br>GO: 42766<br>GO: 6355<br>GO: 6350 | GO: 3677<br>GO: 5488<br>GO: 5515<br>GO: 16563 | GO: 16514<br>GO: 5622<br>GO: 5634 |
| miR-221 | PDCD10 | Hs.478150 | 4 | | GO: 6915 | | |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-221 | PPP6C | Hs.495128 | 4 | | GO: 82 GO: 6470 | GO: 16787<br>GO: 5506<br>GO: 30145<br>GO: 46872<br>GO: 4722 | |
| miR-221 | PLEKHC1 | Hs.509343 | 4 | | GO: 30036<br>GO: 7155<br>GO: 8360 | GO: 5515 | GO: 5856<br>GO: 1725 |
| miR-221 | RBM24 | Hs.519904 | 4 | | | | |
| miR-221 | MEIS1 | Hs.526754 | 4 | | GO: 6355 | GO: 3702<br>GO: 3700 | GO: 5634 |
| miR-221 | HECTD2 | Hs.535293 | 4 | | GO: 15671<br>GO: 6512 | GO: 20037<br>GO: 5344<br>GO: 4842 | GO: 5622 |
| miR-221 | GNAI2 | Hs.77269 | 4 | Axon guidance 04360; Gap junction 04540; Tight junction 04530 | GO: 7186<br>GO: 7194<br>GO: 7584<br>GO: 7165 | GO: 5525<br>GO: 3924<br>GO: 166<br>GO: 4871 | |
| miR-221 | CDKN1C | Hs.106070 | 3 | Cell cycle 04110 | GO: 80 GO: 7049<br>GO: 7050<br>GO: 8285 GO: 79 | GO: 4861<br>GO: 5515 | GO: 5634 |
| miR-221 | GARNL1 | Hs.113150 | 3 | | | GO: 5096 | GO: 5634 |
| miR-221 | MIA3 | Hs.118474 | 3 | | GO: 6096 | GO: 166<br>GO: 4618 | |
| miR-221 | ARNT | Hs.131494 | 3 | | GO: 60 GO: 6355<br>GO: 7165 | GO: 5061<br>GO: 5515<br>GO: 4872<br>GO: 4871<br>GO: 3713<br>GO: 3700<br>GO: 16563 | GO: 5634 |
| miR-221 | ITGA6 | Hs.133397 | 3 | Integrin-mediated cell adhesion | | | |
| miR-221 | GPRC5B | Hs.148685 | 3 | GPCRDB Class C Metabotropic glutamate pheromone | GO: 7186<br>GO: 7165<br>GO: 7601 | GO: 8067<br>GO: 4872<br>GO: 5118 | GO: 16021<br>GO: 16020 |
| miR-221 | CDC2L6 | Hs.159118 | 3 | | | | |
| miR-221 | EIF5A2 | Hs.164144 | 3 | | | | |
| miR-221 | CD4 | Hs.17483 | 3 | Cell adhesion molecules 04514; Hematopoietic cell lineage 04640; T cell receptor signaling pathway 04660 | GO: 30217<br>GO: 45058<br>GO: 7155<br>GO: 6955<br>GO: 45086<br>GO: 7169 | GO: 42289<br>GO: 15026<br>GO: 5515<br>GO: 4888<br>GO: 8270 | GO: 42101<br>GO: 16021<br>GO: 5886 |
| miR-221 | GABRA1 | Hs.175934 | 3 | Neuroactive ligand-receptor interaction 04080 | GO: 6821<br>GO: 7214<br>GO: 6811 | GO: 4890<br>GO: 5230<br>GO: 5216<br>GO: 30594 | GO: 5887<br>GO: 45211 |
| miR-221 | C1QDC1 | Hs.234355 | 3 | | | | |
| miR-221 | CDKN1B | Hs.238990 | 3 | Cell cycle 04110 | GO: 7050<br>GO: 8285 GO: 79 | GO: 4861<br>GO: 5515<br>GO: 5072 | GO: 5737<br>GO: 5634 |
| miR-221 | TRPS1 | Hs.253594 | 3 | | GO: 6607<br>GO: 6355<br>GO: 1501<br>GO: 6350<br>GO: 6366 | GO: 46872<br>GO: 3700<br>GO: 8270 | GO: 5634 |
| miR-221 | DNAJC14 | Hs.253844 | 3 | | | | |
| miR-221 | PGGT1B | Hs.254006 | 3 | | GO: 18348 | GO: 4662<br>GO: 46872<br>GO: 4659<br>GO: 16740<br>GO: 8270 | GO: 5953 |
| miR-221 | MYO1C | Hs.286226 | 3 | | | GO: 5524<br>GO: 3779<br>GO: 5516<br>GO: 3774<br>GO: 166 | GO: 16459<br>GO: 16461 |
| miR-221 | SEC24B | Hs.292472 | 3 | | GO: 6888<br>GO: 6886<br>GO: 16192 | GO: 5515<br>GO: 5215 | GO: 30127<br>GO: 5795<br>GO: 5783<br>GO: 16020 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-221 | RAB1A | Hs.310645 | 3 | | GO: 6888<br>GO: 15031<br>GO: 7264 | GO: 5525<br>GO: 166 | GO: 5795<br>GO: 5783 |
| miR-221 | ASB7 | Hs.31845 | 3 | | GO: 7242 | | |
| miR-221 | LOC145758 | Hs.31845 | 3 | | | | |
| miR-221 | ZFHX1B | Hs.34871 | 3 | TGF Beta Signaling Pathway | | | |
| miR-221 | HRB | Hs.352962 | 3 | | GO: 6406<br>GO: 43087<br>GO: 6810 | GO: 3677<br>GO: 3723<br>GO: 46872<br>GO: 5515<br>GO: 8270 | GO: 5643<br>GO: 5634 |
| miR-221 | EXOC8 | Hs.356198 | 3 | | | | |
| miR-221 | CTCF | Hs.368367 | 3 | | GO: 45786<br>GO: 122<br>GO: 45893<br>GO: 6350 | GO: 3702<br>GO: 46872<br>GO: 3676<br>GO: 3714<br>GO: 3700<br>GO: 8270 | GO: 5634 |
| miR-221 | MYO1E | Hs.370392 | 3 | | GO: 30048 | GO: 5524<br>GO: 42623<br>GO: 3779<br>GO: 5516<br>GO: 146 GO: 166 | GO: 16459 |
| miR-221 | PRDM2 | Hs.371823 | 3 | | GO: 6355 | GO: 46872<br>GO: 3676<br>GO: 3700<br>GO: 8270 | GO: 5634 |
| miR-221 | APG7L | Hs.373959 | 3 | | | | |
| miR-221 | ATG7 | Hs.373959 | 3 | | | | |
| miR-221 | VGLL4 | Hs.373959 | 3 | | GO: 6355<br>GO: 6350 | | GO: 5634 |
| miR-221 | IRF2 | Hs.374097 | 3 | Apoptosis | GO: 8283<br>GO: 6955<br>GO: 122<br>GO: 6355<br>GO: 6350 | GO: 3702<br>GO: 3700 | GO: 5634 |
| miR-221 | DAPK1 | Hs.380277 | 3 | | GO: 6915<br>GO: 8624<br>GO: 6468<br>GO: 7243<br>GO: 7165 | GO: 5524<br>GO: 4685<br>GO: 5516<br>GO: 4684<br>GO: 166<br>GO: 4674<br>GO: 16740 | GO: 15629 |
| miR-221 | BMF | Hs.386140 | 3 | Apoptosis 109581 | GO: 6915 | GO: 5515 | GO: 16459 |
| miR-221 | PAIP2 | Hs.396644 | 3 | | GO: 45947<br>GO: 6445 | GO: 5515<br>GO: 30371 | GO: 5737 |
| miR-221 | EIF3S1 | Hs.404056 | 3 | Gene Expression 74160; Translation 72766 | GO: 6412<br>GO: 6446 | GO: 5515<br>GO: 3743 | GO: 5852 |
| miR-221 | OGT | Hs.405410 | 3 | Blood group glycolipid biosynthesis-lactoseries 00601; Blood group glycolipid biosynthesis-neolactoseries 00602; Fructose and mannose metabolism 00051; Ganglioside biosynthesis 00604; Globoside metabolism 00603; Glycerolipid metabolism 00561; Glycosphingolipid metabolism 00600; High-mannose type N-glycan biosynthesis 00513; N-Glycan biosynthesis 00510; O-Glycan biosynthesis 00512 | GO: 6493<br>GO: 7584<br>GO: 7165 | GO: 8375<br>GO: 5488<br>GO: 5515<br>GO: 16757 | GO: 5829<br>GO: 5634 |
| miR-221 | CPNE8 | Hs.40910 | 3 | | | | |
| miR-221 | PBX3 | Hs.428027 | 3 | | GO: 7387<br>GO: 9790<br>GO: 30902 | GO: 5515<br>GO: 3700 | GO: 5634 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-221 | ZFPM2 | Hs.431009 | 3 | | GO: 7388<br>GO: 6355<br>GO: 45898<br>GO: 6357<br>GO: 6350 | GO: 3677<br>GO: 3702<br>GO: 46872<br>GO: 3714<br>GO: 8270 | GO: 5634 |
| miR-221 | ANKHD1 | Hs.434219 | 3 | Translation Factors | | | |
| miR-221 | RIMS3 | Hs.434924 | 3 | | GO: 6887<br>GO: 6836 | | GO: 45202 |
| miR-221 | ATXN1 | Hs.434961 | 3 | | | GO: 3723 | GO: 5737<br>GO: 5634 |
| miR-221 | EPB41L1 | Hs.437422 | 3 | | | | |
| miR-221 | POLH | Hs.439153 | 3 | | | GO: 3723 | GO: 5737<br>GO: 5634 |
| miR-221 | HOXC10 | Hs.44276 | 3 | | GO: 9653<br>GO: 8284<br>GO: 6355 | GO: 3702<br>GO: 3700 | GO: 5634 |
| miR-221 | Transcribed locus | Hs.446484 | 3 | | | | |
| miR-221 | IQCK | Hs.460217 | 3 | | | | |
| miR-221 | OSBPL7 | Hs.463320 | 3 | | GO: 6869<br>GO: 8202 | GO: 3676 | |
| miR-221 | DOCK10 | Hs.46578 | 3 | | | GO: 5525<br>GO: 51020<br>GO: 5488<br>GO: 5085<br>GO: 4872 | |
| miR-221 | MYO10 | Hs.481720 | 3 | | GO: 7165 | GO: 5524<br>GO: 3779<br>GO: 3774<br>GO: 166 | GO: 5856<br>GO: 16459 |
| miR-221 | PAIP1 | Hs.482038 | 3 | Translation Factors | GO: 48255<br>GO: 45946<br>GO: 6413 | GO: 3723<br>GO: 5515<br>GO: 8494 | GO: 5737 |
| miR-221 | PAIP1 | Hs.482038 | 3 | Translation Factors | | | |
| miR-221 | MYLIP | Hs.484738 | 3 | Tryptophan metabolism 00380 | GO: 6928<br>GO: 7399<br>GO: 16567 | GO: 8092<br>GO: 16874<br>GO: 46872<br>GO: 4842<br>GO: 8270 | GO: 5737<br>GO: 5856<br>GO: 16020<br>GO: 151 |
| miR-221 | POGZ | Hs.489873 | 3 | | GO: 7275 | GO: 3677<br>GO: 46872<br>GO: 3676<br>GO: 8270 | GO: 5634 |
| miR-221 | VDAC3 | Hs.491597 | 3 | Calcium signaling pathway 04020 | GO: 15853<br>GO: 6820 | GO: 15482<br>GO: 8308 | GO: 5887<br>GO: 5741<br>GO: 5739 |
| miR-221 | PLS3 | Hs.496622 | 3 | | | GO: 3779<br>GO: 5509<br>GO: 5515 | GO: 15629 |
| miR-221 | NAV1 | Hs.497369 | 3 | | GO: 6306<br>GO: 6810 | GO: 5524<br>GO: 3677<br>GO: 17111<br>GO: 166 | |
| miR-221 | KCNK2 | Hs.497745 | 3 | | GO: 6811<br>GO: 6813 | GO: 3824<br>GO: 5216<br>GO: 15271<br>GO: 5267<br>GO: 30955<br>GO: 5244 | GO: 16021<br>GO: 16020 |
| miR-221 | INA | Hs.500916 | 3 | | | | |
| miR-221 | GALNTL4 | Hs.501911 | 3 | O-Glycan biosynthesis 00512 | | GO: 5509<br>GO: 30145<br>GO: 4653<br>GO: 5529<br>GO: 16740<br>GO: 16757 | GO: 5795<br>GO: 16021 |
| miR-221 | QKI | Hs.510324 | 3 | | | GO: 3676 | |
| miR-221 | YWHAG | Hs.520974 | 3 | Cell cycle 04110 | GO: 7010<br>GO: 43066<br>GO: 6469 | GO: 3779<br>GO: 5159<br>GO: 19904 | GO: 5737 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| | | | | | GO: 7088 | GO: 42803 | |
| | | | | | GO: 45664 | GO: 5080 | |
| | | | | | GO: 9966 | GO: 8426 | |
| | | | | | GO: 48167 | | |
| miR-221 | ANGPTL2 | Hs.521731 | 3 | | GO: 7275 | GO: 5102 | GO: 5615 |
| miR-221 | TP53BP2 | Hs.523968 | 3 | | GO: 6915 GO: 74 | GO: 5070 | GO: 5737 |
| | | | | | GO: 7165 | GO: 5515 | |
| miR-221 | VASH1 | Hs.525479 | 3 | | GO: 7049 | | |
| | | | | | GO: 7050 | | |
| miR-221 | PPARGC1A | Hs.527078 | 3 | Adipocytokine signaling pathway 04920; Insulin signaling pathway 04910 | GO: 8380 | GO: 3677 | GO: 5665 |
| | | | | | GO: 30521 | GO: 3723 | GO: 5634 |
| | | | | | GO: 50873 | GO: 16455 | |
| | | | | | GO: 1678 | GO: 50681 | |
| | | | | | GO: 45333 | GO: 30374 | |
| | | | | | GO: 7586 | GO: 166 | |
| | | | | | GO: 19395 | GO: 8134 | |
| | | | | | GO: 6094 | | |
| | | | | | GO: 6397 | | |
| | | | | | GO: 7005 | | |
| | | | | | GO: 46321 | | |
| | | | | | GO: 45722 | | |
| | | | | | GO: 35066 | | |
| | | | | | GO: 45893 | | |
| | | | | | GO: 6461 | | |
| | | | | | GO: 50821 | | |
| | | | | | GO: 42594 | | |
| | | | | | GO: 1659 | | |
| | | | | | GO: 6350 | | |
| | | | | | GO: 6367 | | |
| miR-221 | SOCS3 | Hs.527973 | 3 | Adipocytokine signaling pathway 04920; Insulin signaling pathway 04910; Jak-STAT signaling pathway 04630; Type II diabetes mellitus 04930 | GO: 7259 | GO: 4860 | |
| | | | | | GO: 6916 | | |
| | | | | | GO: 7242 | | |
| | | | | | GO: 9968 | | |
| | | | | | GO: 1558 | | |
| miR-221 | HIPK1 | Hs.532363 | 3 | | GO: 6468 | GO: 5524 | GO: 5634 |
| | | | | | GO: 6355 | GO: 16301 | |
| | | | | | GO: 6350 | GO: 166 | |
| | | | | | | GO: 5515 | |
| | | | | | | GO: 4674 | |
| | | | | | | GO: 16740 | |
| miR-221 | GNB3 | Hs.534315 | 3 | Energy Metabolism 163685 | GO: 7186 | GO: 3924 | GO: 5834 |
| | | | | | GO: 8217 | GO: 4871 | |
| | | | | | GO: 7165 | | |
| miR-221 | TFR2 | Hs.544932 | 3 | | GO: 6879 | GO: 8233 | GO: 5887 |
| | | | | | GO: 6826 | GO: 4872 | |
| | | | | | GO: 6508 | GO: 4998 | |
| miR-221 | SLC4A4 | Hs.5462 | 3 | | GO: 6820 | GO: 5452 | GO: 16021 |
| | | | | | GO: 6810 | GO: 8510 | GO: 5887 |
| | | | | | | | GO: 16020 |
| miR-221 | MAGI1 | Hs.567389 | 3 | Dentatorubropallidoluysian atrophy 05050; Tight junction 04530 | GO: 7155 | GO: 5524 | GO: 5886 |
| | | | | | GO: 7166 | GO: 16301 | GO: 5923 |
| | | | | | GO: 6461 | GO: 166 | |
| | | | | | | GO: 8022 | |
| | | | | | | GO: 16740 | |
| miR-221 | PAIP1 | Hs.567929 | 3 | Translation Factors | | | |
| miR-221 | ADAM11 | Hs.6088 | 3 | | GO: 7229 | GO: 5178 | GO: 16021 |
| | | | | | GO: 6508 | GO: 4222 | GO: 5886 |
| miR-221 | RALA | Hs.6906 | 3 | | GO: 6935 | GO: 5525 | |
| | | | | | GO: 6886 | GO: 166 | |
| | | | | | GO: 7165 | GO: 5515 | |
| | | | | | GO: 7264 | | |
| miR-221 | PSMD8 | Hs.78466 | 3 | Proteasome 03050; Cell Cycle 69278; Cell Cycle Checkpoints 69620; DNA Replication 69306 | GO: 6508 GO: 74 | | GO: 5829 |
| | | | | | | | GO: 5838) |
| miR-221 | ANGPTL4 | Hs.9613 | 3 | | GO: 1525 | GO: 4857 | GO: 5576 |
| | | | | | GO: 30154 | | |
| | | | | | GO: 9267 | | |
| | | | | | GO: 43066 | | |
| | | | | | GO: 51005 | | |
| | | | | | GO: 45766 | | |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-221 | FAM13A1 | Hs.97270 | 3 | | GO: 45834<br>GO: 1666 | | |
| miR-221 | NTF3 | Hs.99171 | 3 | MAPK signaling pathway 04010 | GO: 6916<br>GO: 6928<br>GO: 7267<br>GO: 7399<br>GO: 7165 | GO: 8083 | |
| miR-221 | RSBN1L | Hs592289 | 3 | | | | |
| miR-137 | SON | Hs.517262 | 5 | | GO: 6916 | GO: 3677<br>GO: 3725<br>GO: 3676 | GO: 8372<br>GO: 5622<br>GO: 5634 |
| miR-137 | ARID4B | Hs.533633 | 4 | | | GO: 3677<br>GO: 3676 | GO: 5622 |
| miR-137 | CA7 | Hs.37014 | 4 | Nitrogen metabolism 00910 | GO: 6730 | GO: 4089<br>GO: 16829<br>GO: 46872<br>GO: 8270 | |
| miR-137 | CADPS | Hs.127013 | 4 | | GO: 6887 | | GO: 5829 |
| miR-137 | CLPX | Hs.113823 | 4 | | GO: 6457<br>GO: 15031 | GO: 5524<br>GO: 42623<br>GO: 46872<br>GO: 166<br>GO: 51082<br>GO: 8270 | GO: 5739 |
| miR-137 | COCH | Hs.21016 | 4 | | GO: 7605 | | |
| miR-137 | CPNE8 | Hs.40910 | 4 | | | | |
| miR-137 | CPSF6 | Hs.369606 | 4 | | GO: 6397 | GO: 3723<br>GO: 166 | GO: 5634 |
| miR-137 | DHX40 | Hs.29403 | 4 | | | | |
| miR-137 | DUSP4 | Hs.417962 | 4 | MAPK signaling pathway 04010 | GO: 165<br>GO: 6470 GO: 74 | GO: 17017<br>GO: 16787<br>GO: 4725<br>GO: 8330 | GO: 5634 |
| miR-137 | EPHA7 | Hs.73962 | 4 | Axon guidance 04360 | GO: 6468<br>GO: 7169 | GO: 5524<br>GO: 5003<br>GO: 166<br>GO: 5515<br>GO: 4872<br>GO: 16740 | GO: 16021<br>GO: 16020 |
| miR-137 | ESRRA | Hs.110849 | 4 | Nuclear Receptors | GO: 6355<br>GO: 6350 | GO: 46872<br>GO: 5496<br>GO: 3707<br>GO: 3700<br>GO: 8270 | GO: 5634 |
| miR-137 | FKBP4 | Hs.524183 | 4 | Calcium signaling pathway | GO: 6457 | GO: 5528<br>GO: 16853<br>GO: 3755<br>GO: 30674 | GO: 5737<br>GO: 5634 |
| miR-137 | FURIN | Hs.513153 | 4 | Notch Signaling Pathway 157118; Post-translational modification of proteins 163841 | GO: 7267<br>GO: 6508 | GO: 5509<br>GO: 4276<br>GO: 8233<br>GO: 4289 | GO: 5794<br>GO: 16021<br>GO: 30140 |
| miR-137 | HLF | Hs.196952 | 4 | | GO: 7275<br>GO: 6355<br>GO: 48511<br>GO: 6350<br>GO: 6366 | GO: 3690 | GO: 5634 |
| miR-137 | HMGN3 | Hs.77558 | 4 | | GO: 4 | GO: 3677<br>GO: 46966 | GO: 785<br>GO: 5634 |
| miR-137 | INPP5A | Hs.523360 | 4 | Inositol phosphate metabolism 00562; Phosphatidylinositol signaling system 04070 | GO: 7154 | GO: 16787<br>GO: 4437<br>GO: 4445 | GO: 16020 |
| miR-137 | NMNAT3 | Hs.208673 | 4 | | | | |
| miR-137 | NY-SAR-41 | Hs.348418 | 4 | | | | |
| miR-137 | PPP3CB | Hs.500067 | 4 | Apoptosis 04210; Axon guidance 04360; B cell receptor signaling pathway 04662; Calcium signaling pathway | GO: 6470 GO: 74<br>GO: 7165<br>GO: 6351 | GO: 5509<br>GO: 5516<br>GO: 16787<br>GO: 5506<br>GO: 4722 | GO: 5955 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| | | | | 04020; MAPK signaling pathway 04010; Natural killer cell mediated cytotoxicity 04650; T cell receptor signaling pathway 04660; Wnt signaling pathway 04310 | | GO: 8270 | |
| miR-137 | PTPN2 | Hs.123352 | 4 | Calcium signaling pathway; Type I diabetes mellitus | GO: 6470 | GO: 16787 GO: 4725 GO: 4872 | |
| miR-137 | SYT1 | Hs.310545 | 4 | | | | |
| miR-137 | TDRD7 | Hs.193842 | 4 | | | | |
| miR-137 | WIF1 | Hs.284122 | 4 | Wnt signaling pathway 04310 | GO: 16055 GO: 7267 GO: 7275 GO: 7165 | GO: 4713 | |
| miR-137 | ZC3H6 | Hs.190477 | 4 | | | | |
| miR-137 | ABHD6 | Hs.476454 | 3 | | GO: 6725 | GO: 16787 | |
| miR-137 | ACSL6 | Hs.14945 | 3 | Adipocytokine signaling pathway 04920; Fatty acid metabolism 00071 | GO: 6637 GO: 6629 GO: 8152 | GO: 16874 GO: 4467 GO: 287 | GO: 16021 GO: 5792 GO: 5741 GO: 5778 GO: 5886 |
| miR-137 | ACVR1 | Hs.470316 | 3 | Cytokine-cytokine receptor interaction 04060; TGF-beta signaling pathway 04350 | GO: 6468 GO: 7178 | GO: 5524 GO: 287 GO: 30145 GO: 166 GO: 4713 GO: 4872 GO: 16740 GO: 5024 | GO: 5887 GO: 16020 |
| miR-137 | AP3S1 | Hs.406191 | 3 | | GO: 8286 GO: 6886 GO: 6810 | GO: 5215 | GO: 5795 GO: 30125 GO: 30119 GO: 30133 |
| miR-137 | ATBF1 | Hs.569686 | 3 | | | | |
| miR-137 | ATP1B1 | Hs.291196 | 3 | Calcium regulation in cardiac cells; Purine metabolism | GO: 6813 GO: 6814 GO: 6810 | GO: 30955 GO: 31402 GO: 5391 | GO: 16021 GO: 16020 GO: 5890 |
| miR-137 | ATXN1 | Hs.434961 | 3 | | | | |
| miR-137 | POLH | Hs.439153 | 3 | | | GO: 3723 | GO: 5737 GO: 5634 |
| miR-137 | BACH2 | Hs.269764 | 3 | | GO: 6355 GO: 6350 | GO: 3677 GO: 5515 | GO: 5634 |
| miR-137 | C5orf13 | Hs.483067 | 3 | | | | |
| miR-137 | CABLES2 | Hs.301040 | 3 | | | | |
| miR-137 | CACNA1G | Hs.194746 | 3 | Calcium signaling pathway 04020; Type II diabetes mellitus 04930 | GO: 6816 GO: 6812 | GO: 5509 GO: 5261 GO: 8332 GO: 5245 | GO: 16021 GO: 16020 GO: 5624 GO: 5891 |
| miR-137 | CHES1 | Hs.434286 | 3 | | GO: 77 GO: 85 GO: 6355 GO: 6350 | GO: 5515 GO: 3700 | GO: 5634 |
| miR-137 | CHST9 | Hs.567604 | 3 | Cysteine metabolism 00272 | GO: 5975 GO: 7417 GO: 30203 GO: 42446 GO: 6790 | GO: 1537 GO: 16740 | GO: 5795 GO: 16021 GO: 31228 |
| miR-137 | CRSP2 | Hs.407604 | 3 | | GO: 30521 GO: 45944 GO: 6350 GO: 6367 | GO: 16455 GO: 30374 GO: 4872 GO: 46966 GO: 42809 | GO: 119 GO: 5634 |
| miR-137 | CSDA | Hs.221889 | 3 | Tight junction 04530 | GO: 122 GO: 6355 GO: 9409 GO: 6350 | GO: 3677 GO: 3702 GO: 3690 GO: 3714 GO: 3700 | GO: 5737 GO: 5634 |
| miR-137 | CSE1L | Hs.90073 | 3 | | GO: 6915 GO: 8283 GO: 59 GO: 15031 | GO: 5488 GO: 8262 GO: 8565 | GO: 5737 GO: 5643 GO: 5634 |
| miR-137 | CUL3 | Hs.372286 | 3 | Ubiquitin mediated proteolysis 04120 | GO: 82 GO: 7049 GO: 7050 | GO: 5515 | GO: 5634 |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-137 | DCDC2 | Hs.512603 | 3 | | GO: 8629<br>GO: 8284<br>GO: 6512<br>GO: 6968<br>GO: 7242 | | |
| miR-137 | DMRT2 | Hs.59506 | 3 | | GO: 1764<br>GO: 8584<br>GO: 6355<br>GO: 7530<br>GO: 7548<br>GO: 6350 | GO: 46872<br>GO: 3700<br>GO: 8270 | GO: 5634 |
| miR-137 | DUSP8 | Hs.41688 | 3 | MAPK signaling pathway 04010 | GO: 188<br>GO: 6470 | GO: 17017<br>GO: 16787<br>GO: 4725 | GO: 5737<br>GO: 5634 |
| miR-137 | DYRK1A | Hs.368240 | 3 | Benzoate degradation via CoA ligation 00632; Inositol phosphate metabolism 00562; Nicotinate and nicotinamide metabolism 00760; Phosphatidylinositol signaling system 04070 | GO: 7399<br>GO: 18108 | GO: 5524<br>GO: 4715<br>GO: 166<br>GO: 4674<br>GO: 16740 | GO: 5634 |
| miR-137 | EIF2C1 | Hs.22867 | 3 | | GO: 6412<br>GO: 6446 | GO: 5515<br>GO: 3743 | GO: 5850 |
| miR-137 | ENC1 | Hs.104925 | 3 | | GO: 7275<br>GO: 7399 | GO: 3779<br>GO: 5515 | GO: 5856<br>GO: 5634 |
| miR-137 | EPAS1 | Hs.468410 | 3 | | GO: 1525<br>GO: 30154<br>GO: 6355<br>GO: 1666<br>GO: 7165<br>GO: 6366 | GO: 3705<br>GO: 35035<br>GO: 5515<br>GO: 4871<br>GO: 3713 | GO: 5634 |
| miR-137 | EPHA4 | Hs.371218 | 3 | Axon guidance 04360 | GO: 6468<br>GO: 7165<br>GO: 7169 | GO: 5524<br>GO: 5003<br>GO: 166<br>GO: 4674<br>GO: 4872<br>GO: 16740 | GO: 5887<br>GO: 16020 |
| miR-137 | ERG | Hs.473819 | 3 | | GO: 8283<br>GO: 7275<br>GO: 6468<br>GO: 6355<br>GO: 7165<br>GO: 6350 | GO: 5515<br>GO: 4871<br>GO: 3700 | GO: 5634 |
| miR-137 | ESRRG | Hs.444225 | 3 | | GO: 7275<br>GO: 45893<br>GO: 6350 | GO: 50682<br>GO: 5516<br>GO: 46872<br>GO: 5496<br>GO: 3707<br>GO: 3700<br>GO: 16563<br>GO: 8270 | GO: 5634 |
| miR-137 | FAM77C | Hs.470259 | 3 | | | | |
| miR-137 | GABRA1 | Hs.175934 | 3 | Neuroactive ligand-receptor interaction 04080 | GO: 6821<br>GO: 7214<br>GO: 6811 | GO: 4890<br>GO: 5230<br>GO: 5216<br>GO: 30594 | GO: 5887<br>GO: 45211 |
| miR-137 | GPR85 | Hs.152009 | 3 | GPCRDB Class A Rhodopsin-like | GO: 7186<br>GO: 7165 | GO: 4872<br>GO: 1584 | GO: 16021 |
| miR-137 | GPR88 | Hs.170053 | 3 | GPCRDB Other | GO: 7186<br>GO: 7165 | GO: 16526<br>GO: 4872<br>GO: 1584 | GO: 8372<br>GO: 16021 |
| miR-137 | IFT20 | Hs.4187 | 3 | | | | GO: 19861 |
| miR-137 | ITPR3 | Hs.93235 | 3 | Calcium regulation in cardiac cells; Smooth muscle contraction | | | |
| miR-137 | KIAA2010 | Hs.533887 | 3 | | GO: 15986<br>GO: 6817 | GO: 5488<br>GO: 46933<br>GO: 46961 | GO: 5737<br>GO: 16020<br>GO: 16469 |
| miR-137 | LGR4 | Hs.502176 | 3 | | GO: 7186<br>GO: 7165 | GO: 16500<br>GO: 4872 | GO: 16021 |
| miR-137 | LRRN3 | Hs.3781 | 3 | | | | |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-137 | MITF | Hs.166017 | 3 | | GO: 7275<br>GO: 30318<br>GO: 6355<br>GO: 7605 | GO: 3677<br>GO: 16563 | GO: 5634 |
| miR-137 | MTPN | Hs.43297 | 3 | | | | |
| miR-137 | MYBPC1 | Hs.567306 | 3 | Striated muscle contraction | | | |
| miR-137 | NAB2 | Hs.159223 | 3 | | GO: 8283<br>GO: 16481<br>GO: 7399<br>GO: 6355<br>GO: 6350 | GO: 3714 | GO: 5634 |
| miR-137 | NRP1 | Hs.131704 | 3 | Axon guidance 04360 | GO: 1525<br>GO: 7411<br>GO: 7155<br>GO: 30154<br>GO: 7267<br>GO: 7399<br>GO: 9887<br>GO: 8284<br>GO: 7165 | GO: 4872<br>GO: 5021 | GO: 16021<br>GO: 16020<br>GO: 5624 |
| miR-137 | OXSR1 | Hs.475970 | 3 | Calcium signaling pathway; Phosphatidylinositol signaling system | GO: 6468<br>GO: 7243<br>GO: 6979 | GO: 5524<br>GO: 287 GO: 166<br>GO: 5515<br>GO: 4674<br>GO: 4713<br>GO: 16740 | |
| miR-137 | PDLIM3 | Hs.85862 | 3 | | | GO: 46872<br>GO: 5515<br>GO: 8270 | |
| miR-137 | PHF15 | Hs.483419 | 3 | | GO: 6355 | GO: 5515<br>GO: 8270 | |
| miR-137 | PITPNA | Hs.429819 | 3 | | GO: 6629<br>GO: 6810<br>GO: 7601 | GO: 8289<br>GO: 8525<br>GO: 8526 | GO: 5622 |
| miR-137 | PLEKHA5 | Hs.188614 | 3 | | GO: 4 | GO: 5545 | GO: 8372 |
| miR-137 | PPM1E | Hs.245044 | 3 | ; Calcium signaling pathway | | | |
| miR-137 | PTGFRN | Hs.418093 | 3 | | | | |
| miR-137 | RANBP2 | Hs.199561 | 3 | | GO: 46907<br>GO: 6457<br>GO: 6606 | GO: 8536<br>GO: 5488<br>GO: 16853<br>GO: 46872<br>GO: 3755<br>GO: 8270 | GO: 5643<br>GO: 5634 |
| miR-137 | RBM12 | Hs.246413 | 3 | | | | |
| miR-137 | RPS13 | Hs.446588 | 3 | Ribosome 03010; Gene Expression 74160; Translation 72766 | GO: 6412 | GO: 3735 | GO: 5840 |
| miR-137 | RWDD4A | Hs.133337 | 3 | | | | |
| miR-137 | SGCG | Hs.37167 | 3 | | GO: 7010<br>GO: 7517 | | GO: 5856<br>GO: 16021<br>GO: 5886<br>GO: 16012 |
| miR-137 | SH3BP5 | Hs.257761 | 3 | | GO: 7242 | GO: 17124<br>GO: 5070<br>GO: 5515<br>GO: 4860 | GO: 5739 |
| miR-137 | SIPA1L2 | Hs.268774 | 3 | | | GO: 5096<br>GO: 5515 | |
| miR-137 | SLC17A6 | Hs.242821 | 3 | | | | |
| miR-137 | SLC25A5 | Hs.522767 | 3 | Calcium signaling pathway 04020; Nucleotide metabolism 15869 | GO: 6839<br>GO: 6810 | GO: 15207<br>GO: 5488<br>GO: 5215 | GO: 5887<br>GO: 5743<br>GO: 5739 |
| miR-137 | SLC43A2 | Hs.160550 | 3 | | | | |
| miR-137 | SLC6A15 | Hs.44424 | 3 | | GO: 6836 | GO: 5328<br>GO: 15293 | GO: 5887<br>GO: 16020 |
| miR-137 | SLC7A9 | Hs.408567 | 3 | | GO: 6520<br>GO: 6865<br>GO: 6461<br>GO: 6810 | GO: 15184<br>GO: 5279 | GO: 5887<br>GO: 5886 |
| miR-137 | SNX25 | Hs.369091 | 3 | | GO: 7242 | GO: 4871 | |

TABLE 6-continued

Predicted Target Genes of The microRNAs

| microRNA | Gene Symbol | UniGene | Algorithms* | Pathways† | GO biological process | GO molecular function | GO cellular component |
|---|---|---|---|---|---|---|---|
| miR-137 | SRPK1 | Hs.443861 | 3 | mRNA processing | GO: 30154<br>GO: 7059<br>GO: 398<br>GO: 6468<br>GO: 7243<br>GO: 50684 | GO: 5524<br>GO: 287 GO: 166<br>GO: 5515<br>GO: 4674<br>GO: 16740 | GO: 5737<br>GO: 5634 |
| miR-137 | ST18 | Hs.147170 | 3 | | GO: 6355 | GO: 3700 | GO: 5634 |
| miR-137 | STX16 | Hs.307913 | 3 | SNARE interactions in vesicular transport 04130 | GO: 6891<br>GO: 6886 | GO: 8565<br>GO: 5486 | GO: 5795<br>GO: 16021<br>GO: 16020<br>GO: 5792 |
| miR-137 | SV2A | Hs.516153 | 3 | ECM-receptor interaction 04512 | GO: 6810 | GO: 15293<br>GO: 5215 | GO: 16021<br>GO: 16020 |
| miR-137 | TARDBP | Hs.300624 | 3 | | GO: 7067<br>GO: 398<br>GO: 6355<br>GO: 6350<br>GO: 6366 | GO: 3723<br>GO: 8017<br>GO: 166<br>GO: 5515<br>GO: 3700 | GO: 5634 |
| miR-137 | TBC1D19 | Hs.567531 | 3 | | | GO: 5096 | |
| miR-137 | TCF12 | Hs.511504 | 3 | | | | |
| miR-137 | THBS4 | Hs.211426 | 3 | Cell Communication 01430; ECM-receptor interaction 04512; Focal adhesion 04510; TGF-beta signaling pathway 04350; Hemostasis 109582 | GO: 7155<br>GO: 6930 | GO: 5509<br>GO: 8201<br>GO: 5515<br>GO: 5198 | GO: 5578) |
| miR-137 | THRAP1 | Hs.282678 | 3 | | GO: 30521<br>GO: 45944<br>GO: 6355<br>GO: 6350<br>GO: 6367 | GO: 16455<br>GO: 30374<br>GO: 4872<br>GO: 46966<br>GO: 42809 | GO: 119<br>GO: 5634 |
| miR-137 | TRPS1 | Hs.253594 | 3 | | GO: 6607<br>GO: 6355<br>GO: 1501<br>GO: 6350<br>GO: 6366 | GO: 46872<br>GO: 3700<br>GO: 8270 | GO: 5634 |
| miR-137 | TSSK3 | Hs.512763 | 3 | | GO: 30154<br>GO: 7242<br>GO: 6468<br>GO: 48240<br>GO: 7283 | GO: 5524<br>GO: 166<br>GO: 4674<br>GO: 4713<br>GO: 16740 | GO: 5622 |
| miR-137 | UGP2 | Hs.516217 | 3 | Galactose metabolism 00052; Nucleotide sugars metabolism 00520; Pentose and glucuronate interconversions 00040; Starch and sucrose metabolism 00500; Metabolism of sugars 71387 | GO: 6011<br>GO: 8152 | GO: 3983<br>GO: 16301<br>GO: 16740 | |

*Predicted by at least three of five algorithms (PicTar, TargetScan, Miranda, MirBase, and CRSD)
†Analyzed according to KEGG (http://www.genome.jp/kegg/), GenMAPP (http://www..org/), and Reactome (http://www.reactome.org/)

TABLE 7

Predicted Pathways Affected By The microRNAs

| Pathway* | microRNA | No. Predicted Targets† | P value† |
|---|---|---|---|
| MAPK signaling pathway | hsa-let-7a | 55 | 9.0E−24 |
| | hsa-miR-372 | 22 | 5.5E−06 |
| | hsa-miR-182* | 9 | 3.0E−05 |
| | hsa-miR-221 | 15 | 4.1E−04 |
| | hsa-miR-137 | 13 | 1.7E−03 |
| Adipocytokine signaling pathway | hsa-miR-182* | 6 | 2.7E−06 |
| | hsa-miR-221 | 9 | 8.6E−06 |
| | hsa-miR-137 | 6 | 1.5E−03 |
| | hsa-miR-372 | 7 | 2.3E−03 |
| | hsa-let-7a | 6 | 4.2E−02 |

TABLE 7-continued

Predicted Pathways Affected By The microRNAs

| Pathway* | microRNA | No. Predicted Targets† | P value† |
|---|---|---|---|
| VEGF signaling pathway | hsa-miR-372 | 11 | 5.2E−06 |
| | hsa-miR-182* | 5 | 7.0E−05 |
| | hsa-let-7a | 9 | 2.0E−03 |
| | hsa-miR-137 | 4 | 4.6E−02 |
| Wnt signaling pathway | hsa-miR-372 | 22 | 4.3E−10 |
| | hsa-let-7a | 21 | 8.3E−07 |
| | hsa-miR-182* | 6 | 3.2E−04 |
| | hsa-miR-221 | 8 | 1.4E−02 |
| Type II diabetes mellitus | hsa-miR-221 | 6 | 2.6E−04 |
| | hsa-miR-137 | 5 | 1.3E−03 |
| | hsa-let-7a | 7 | 1.5E−03 |
| | hsa-miR-182* | 3 | 2.2E−03 |
| Focal adhesion | hsa-let-7a | 37 | 3.2E−13 |
| | hsa-miR-182* | 5 | 1.1E−02 |
| | hsa-miR-221 | 10 | 1.8E−02 |
| Adherens junction | hsa-let-7a | 16 | 1.3E−05 |
| | hsa-miR-221 | 6 | 3.1E−02 |
| | hsa-miR-372 | 7 | 4.0E−02 |
| Axon guidance | hsa-miR-137 | 20 | 3.1E−12 |
| | hsa-let-7a | 26 | 6.2E−11 |
| | hsa-miR-372 | 19 | 1.4E−08 |
| B cell receptor signaling pathway | hsa-miR-372 | 11 | 9.6E−07 |
| | hsa-let-7a | 12 | 4.5E−06 |
| | hsa-miR-137 | 4 | 2.7E−02 |
| Calcium signaling pathway | hsa-miR-372 | 22 | 1.0E−08 |
| | hsa-let-7a | 25 | 7.6E−08 |
| | hsa-miR-137 | 11 | 7.5E−04 |
| Cell cycle | hsa-miR-372 | 17 | 3.5E−09 |
| | hsa-miR-221 | 9 | 2.4E−04 |
| | hsa-let-7a | 9 | 1.7E−02 |
| ECM-receptor interaction | hsa-let-7a | 27 | 6.0E−16 |
| | hsa-miR-372 | 9 | 1.1E−03 |
| | hsa-miR-182* | 4 | 2.3E−03 |
| Epithelial cell signaling in Helicobacter pylori infection | hsa-miR-221 | 7 | 6.1E−05 |
| | hsa-miR-182* | 4 | 2.0E−04 |
| | hsa-let-7a | 5 | 3.9E−02 |
| Insulin signaling pathway | hsa-miR-221 | 9 | 1.6E−03 |
| | hsa-miR-182* | 4 | 7.8E−03 |
| | hsa-let-7a | 10 | 3.2E−02 |
| Long-term potentiation | hsa-miR-372 | 12 | 1.6E−06 |
| | hsa-let-7a | 12 | 5.1E−05 |
| | hsa-miR-137 | 5 | 1.5E−02 |

*Listed only which are regulated by at least three of five microRNAs selected in this study
†Analyzed by GeneSpring software (f) Kaplan-Meier Survival Analysis of a 3-microRNA Signature Applying Kaplan-Meier survival analysis, a 3-microRNA signature, composed of hsa-miR221, hsa-miR372, and hsa-miR137, was also found to be associated with patients' post-treatment survival. As shown below, this result is statistically significant.

Training Dataset (n=56):
  In overall survival analysis, P value=0.0013
  In relapse-free survival analysis, P value=0.0437

Testing Dataset (n=56):
  In overall survival analysis, P value=0.1468
  In relapse-free survival analysis, P value=0.0841

Independent Cohort (n=62):
  In overall survival analysis, P value=0.0359
  In relapse-free survival analysis, P value=0.0985

Training Dataset and Testing Dataset (n=112):
  In overall survival, P value=0.0011
  In relapse-free survival, P value=0.0119

The P values were obtained from log-rank test for testing different survival curves between high and low risk groups of patients.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to oxadiazole compounds described above also can be made, screened for the above-described activities and used to practice this invention. Thus, other embodiments are also within the claims.

What is claimed is:

1. A method of predicting post-treatment survival of a lung cancer patient, comprising
   detecting expression levels of microRNAs hsa-miR137, hsa-miR372, hsa-miR182*, hsa-miR221, and hsa-let-7a in a lung cancer patient who has been subjected to treatment;
   calculating a risk score of the patient based on the expression levels of these microRNAs; and
   determining prospect of post-treatment survival based on the value of the risk score.

2. The method of claim 1, wherein the risk score is calculated as follows:

(0.15×expression level of hsa-miR137)+(0.31×expression level of hsa-miR372)+(0.28×expression level of hsa-miR182*)+(−0.13×expression level of hsa-miR221)+(−0.14×expression level of hsa-let-7a).

3. The method of claim 2, wherein a risk score equal to or lower than −7.1 indicates that the patient has a fair prospect of post-treatment survival.

4. The method of claim 1, wherein the patient has non-small cell lung cancer.

5. The method of claim 4, wherein the patient is in stage I, II, or III of the non-small cell lung cancer.

6. The method of claim 1, wherein the patient has been subjected to surgical treatment, chemical treatment, radiotherapy, or a combination thereof.

* * * * *